United States Patent
Futami et al.

(10) Patent No.: US 10,822,384 B2
(45) Date of Patent: Nov. 3, 2020

(54) METHOD FOR PRODUCING REAGENT FOR ANTIBODY DETECTION AND USE THEREOF

(71) Applicants: Junichiro Futami, Okayama (JP); Medinet Co., Ltd., Kanagawa (JP)

(72) Inventors: Junichiro Futami, Okayama (JP); Kazuhiro Kakimi, Tokyo (JP); Ryuji Maekawa, Tokyo (JP); Masato Shiraki, Kanagawa (JP)

(73) Assignees: Junichiro Futami, Okayama (JP); Medinet Co., Ltd., Kanagawa (JP)

( * ) Notice: Subject to any disclaimer, the term of this patent is extended or adjusted under 35 U.S.C. 154(b) by 0 days.

(21) Appl. No.: 14/389,016

(22) PCT Filed: Mar. 29, 2013

(86) PCT No.: PCT/JP2013/059692
§ 371 (c)(1),
(2) Date: Sep. 29, 2014

(87) PCT Pub. No.: WO2013/147233
PCT Pub. Date: Oct. 3, 2013

(65) Prior Publication Data
US 2015/0064801 A1    Mar. 5, 2015

(30) Foreign Application Priority Data
Mar. 30, 2012    (JP) ................. 2012-082735

(51) Int. Cl.
| | | |
|---|---|---|
| *C07K 17/00* | (2006.01) | |
| *G01N 33/543* | (2006.01) | |
| *C07K 14/47* | (2006.01) | |
| *G01N 33/574* | (2006.01) | |
| *G01N 33/68* | (2006.01) | |
| *C07K 1/113* | (2006.01) | |

(52) U.S. Cl.
CPC .......... *C07K 14/4748* (2013.01); *C07K 1/113* (2013.01); *C07K 14/4703* (2013.01); *G01N 33/543* (2013.01); *G01N 33/574* (2013.01); *G01N 33/57426* (2013.01); *G01N 33/57492* (2013.01); *G01N 33/6854* (2013.01); *G01N 2333/47* (2013.01); *G01N 2333/4704* (2013.01)

(58) Field of Classification Search
CPC .................................................. G01N 33/574
See application file for complete search history.

(56) References Cited

U.S. PATENT DOCUMENTS

| 6,589,736 B1 * | 7/2003 | Rothschild | ......... | A61K 41/0042 |
| | | | | 435/5 |
| 2005/0070028 A1 | 3/2005 | Ito et al. | | |
| 2006/0084165 A1 * | 4/2006 | Lee | ....... | B01F 11/0266 |
| | | | | 435/259 |
| 2007/0072243 A1 * | 3/2007 | Meikle | ............ | A61K 49/0058 |
| | | | | 435/7.2 |
| 2009/0123948 A1 | 5/2009 | Cho-Chung | | |
| 2009/0275066 A1 * | 11/2009 | Popot | ....... | C07K 17/06 |
| | | | | 435/18 |
| 2009/0286330 A1 | 11/2009 | Shigenobu | | |
| 2013/0096278 A1 | 4/2013 | Futami et al. | | |

FOREIGN PATENT DOCUMENTS

| CN | 101551394 A | 10/2009 | | |
|---|---|---|---|---|
| JP | 2008-002961 A | 1/2008 | | |
| WO | WO-2011/118731 A1 * | 9/2011 | ........... | C07C 381/04 |

OTHER PUBLICATIONS

Yamada et al., "An S-Alkylating Reagent with Positive Charges as an Efficient Solubilizer of Denatured Disulfide-Containing Proteins", J. Biochem., vol. 16, pp. 852-857, published 1994.*
Beretta et al., "Antigenic determinants of bovine serum albumin", Int Arch Allergy Immunol., Nov. 2001;126(3):188-95 (print retrieved from NCBI website).*
Okazaki et al., "A Convenient Protein Substrate for the Determination of Protease Specificity: Reduced and S-3-(Trimethylated amino)propylated Lysozyme", Analytical Biochemistry, vol. 145, pp. 87-90. (Year: 1985).*
Ching-Li et al., "Enzymic and Immunochemical Properties of Lysozyme", Biochem. J. (1977), vol. 167, pp. 571-581. (Year: 1977).*
English Abstract for Japanese patent document JP 2005099001, 2 pages.
English Abstract for Japanese patent document JP H0674956, 1 page.
Inoue et al., "A new derivatizing agent, trimethylammoniopropyl methanethiosulphonate, is efficient for preparation of recombinant brain-derived neurotrophic factor from inclusion bodies", *Biotechnol. Appl. Biochem.*, 28, pp. 207-213 (1998).
Seno et al., "Purification and Characterization of a Recombinant Human Cripto-1 Protein", *Growth Factors*, vol. 15, pp. 215-229 (1998), Overseas Publishers Association.
International Search Report regarding PCT/JP2013/059692, dated Jul. 2, 2013, 1 page.
Written Opinion regarding corresponding Singapore Application No. 11201406160Q, dated Nov. 13, 2015, 5 pages.

(Continued)

Primary Examiner — Bao Thuy L Nguyen
Assistant Examiner — Nam P Nguyen
(74) Attorney, Agent, or Firm — Foley & Lardner LLP

(57) ABSTRACT

The present invention provides the following: a method for efficiently producing a reagent for detecting an antibody that specifically binds with an insoluble antigen protein present in a liquid sample; a reagent for antibody detection produced by the production method; and a use of the antibody. In a step for solubilizing an antigen protein, it is possible to efficiently solubilize and recover the antigen protein by using a cationizing agent; therefore, when compared to conventional methods, it is possible to efficiently produce a reagent for detecting an antibody that has bound to multiple antigen protein molecules in a carrier.

13 Claims, 10 Drawing Sheets

Specification includes a Sequence Listing.

(56) References Cited

OTHER PUBLICATIONS

Arvieux, J. et al., "Neutrophil activations by anti-$\beta_2$ glycoprotein I monoclonal antibodies via Fcγ receptor II," J. Leukocyte Biol., 57(3), pp. 387-394 (1995).
Pei, R., et al., "Flow Cytometric Detection of HLA Antibodies Using a Spectrum of Microbeads," Human Immunol., 60(12), pp. 1293-1302 (1999).
Pesce, A.J. et al., "Cationic antigens Problems associated with measurement by ELISA," Immunol. Methods, 87(1), pp. 21-27 (1986).
Written Opinion regarding corresponding Singapore Appl. No. 11201406160Q, dated Apr. 24, 2015, 6 pps.
Chinese Office Action regarding corresponding Chinese Appl. No. 201380028339.6 (and its English translation), dated Jul. 22, 2015, 13 pages.
English abstract of CN1449494(A) published Oct. 15, 2003, 1 page.
English abstract of CN1719256(A) published Jan. 11, 2006, 1 page.
English abstract of CN101403747(A) published Apr. 8, 2009, 1 page.
English abstract of CN101452001(A) published Jun. 10, 2009, 1 page.
Extended European Search Report and Written Opinion regarding European Application No. 13768100.3, dated Oct. 13, 2015, 6 pages.
Abstract of JP 2007 528004 A, published on Oct. 4, 2007, 1 page.
Abstract of JP 2008-233007 A, published Oct. 2, 2008, 1 page.

\* cited by examiner

REDUCED  NON-REDUCED

FIG. 9
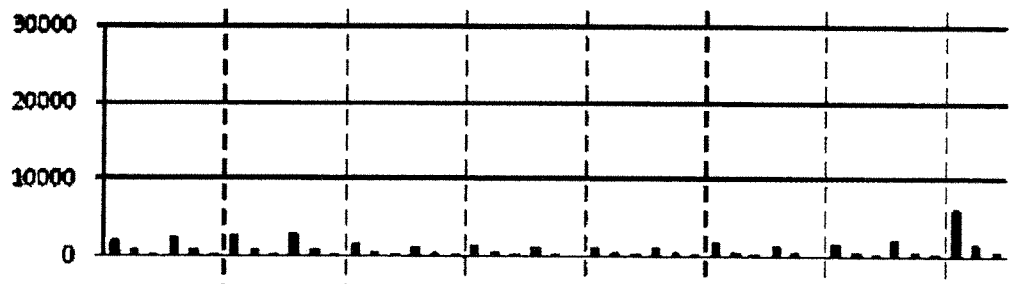
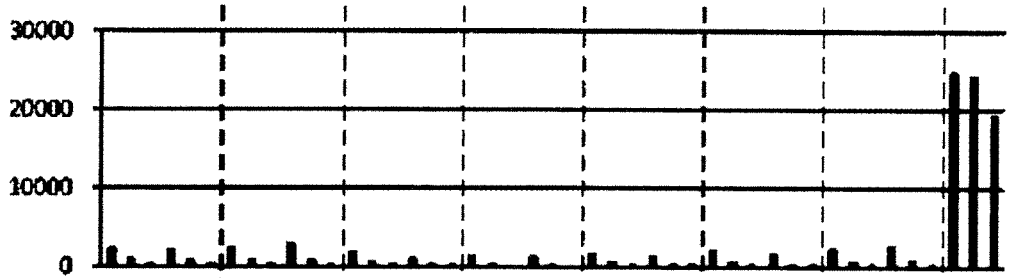
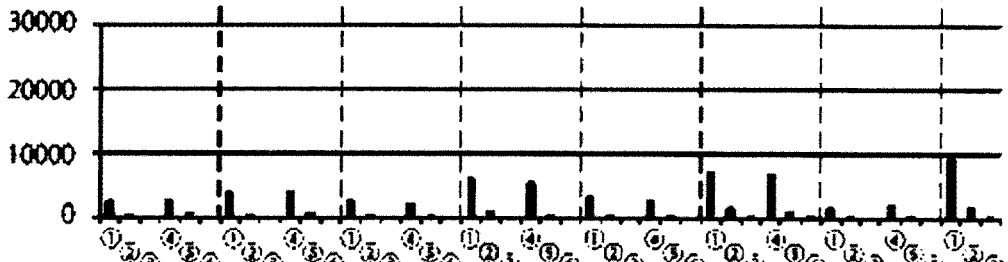
① 400-FOLD DILUTION
② 1600-FOLD DILUTION   BEFORE TREATMENT
③ 6400-FOLD DILUTION
④ 400-FOLD DILUTION
⑤ 1600-FOLD DILUTION   AFTER TREATMENT
⑥ 6400-FOLD DILUTION

SEQUENCE LISTING

```
<160> NUMBER OF SEQ ID NOS: 25

<210> SEQ ID NO 1
<211> LENGTH: 1554
<212> TYPE: DNA
<213> ORGANISM: Homo sapiens

<400> SEQUENCE: 1
atgcaggacc cggcttccac gtgtgtcccg gagccggcgt ctcagcacac gctccgctcc      60
gggcctgggt gcctacagca gccagagcag cagggagtcc gggacccggg cggcatctgg     120
gccaagttag gcgccgccga ggccagcgct gaacgtctcc agggccggag gagccgcggg     180
gcgtccgggt ctgagccgca gcaaatgggc tccgacgtgc gggacctgaa cgcgctgctg     240
cccgccgtcc cctccctggg tggcggcggc ggctgtgccc tgcctgtgag cggcgcggcg     300
cagtgggcgc cggtgctgga ctttgcgccc ccgggcgctt cggcttacgg gtcgttgggc     360
ggccccgcgc cgccaccggc tccgccgcca ccccgcgcg cgccgcctca ctccttcatc     420
aaacaggagc cgagctgggg cggcgcggag ccgcacgagg agcagtgcct gagcgccttc     480
actgtccact tttccggcca gttcactggc acagccggag cctgtcgcta cgggcccttc     540
ggtcctcctc cgcccagcca ggcgtcatcc ggccaggcca ggatgtttcc taacgcgccc     600
tacctgccca gctgcctcga gagccagccc gctattcgca atcagggtta cagcacggtc     660
accttcgacg ggacgcccag ctacggtcac acgccctcgc accatgcggc gcagttcccc     720
aaccactcat tcaagcatga ggatcccatg ggccagcagg gctcgctggg tgagcagcag     780
tactcggtgc cgccccggt ctatggctgc cacacccca ccgacagctg caccggcagc     840
caggctttgc tgctgaggac gccctacagc agtgacaatt tataccaaat gacatcccag     900
cttgaatgca tgacctggaa tcagatgaac ttaggagcca ccttaaaggg agttgctgct     960
gggagctcca gctcagtgaa atggacagaa gggcagagca accacagcac agggtacgag    1020
agcgataacc acacaacgcc catcctctgc ggagcccaat acagaataca cacgcacggt    1080
gtcttcagag gcattcagga tgtgcgacgt gtgcctggag tagccccgac tcttgtacgg    1140
```

-continued

```
tcggcatctg agaccagtga gaaacgcccc ttcatgtgtg cttacccagg ctgcaataag    1200
agatatttta agctgtccca cttacagatg cacagcagga agcacactgg tgagaaacca    1260
taccagtgtg acttcaagga ctgtgaacga aggttttctc gttcagacca gctcaaaaga    1320
caccaaagga gacatacagg tgtgaaacca ttccagtgta aaacttgtca gcgaaagttc    1380
tcccggtccg accacctgaa gacccacacc aggactcata caggtaaaac aagtgaaaag    1440
cccttcagct gtcggtggcc aagttgtcag aaaaagtttg cccggtcaga tgaattagtc    1500
cgccatcaca acatgcatca gagaaacatg accaaactcc agctggcgct ttga          1554
```

<210> SEQ ID NO 2
<211> LENGTH: 517
<212> TYPE: PRT
<213> ORGANISM: Homo sapiens

<400> SEQUENCE: 2

```
Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Ala Pro
        115                 120                 125

Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300
```

```
Thr Trp Asn Gln Met Asn Leu Gly Ala Thr Leu Lys Gly Val Ala Ala
305                 310                 315                 320

Gly Ser Ser Ser Val Lys Trp Thr Glu Gly Gln Ser Asn His Ser
            325                 330                 335

Thr Gly Tyr Glu Ser Asp Asn His Thr Thr Pro Ile Leu Cys Gly Ala
        340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
            405                 410                 415

Gly Glu Lys Pro Tyr Gln Cys Asp Phe Lys Asp Cys Glu Arg Arg Phe
        420                 425                 430

Ser Arg Ser Asp Gln Leu Lys Arg His Gln Arg His Thr Gly Val
        435                 440                 445

Lys Pro Phe Gln Cys Lys Thr Cys Gln Arg Lys Phe Ser Arg Ser Asp
450                 455                 460

His Leu Lys Thr His Thr Arg Thr His Thr Gly Lys Thr Ser Glu Lys
465                 470                 475                 480

Pro Phe Ser Cys Arg Trp Pro Ser Cys Gln Lys Lys Phe Ala Arg Ser
            485                 490                 495

Asp Glu Leu Val Arg His His Asn Met His Gln Arg Asn Met Thr Lys
        500                 505                 510

Leu Gln Leu Ala Leu
        515

<210> SEQ ID NO 3
<211> LENGTH: 954
<212> TYPE: DNA
<213> ORGANISM: Homo sapiens

<400> SEQUENCE: 3
atgtcttctg agcagaagag tcagcactgc aagcctgagg aaggcgttga ggcccaagaa      60
gaggccctgg gcctggtggg tgcgcaggct cctactactg aggagcagga ggctgctgtc     120
tcctcctcct ctcctctggt ccctggcacc ctggaggaag tgcctgctgc tgagtcagca     180
ggtcctcccc agagtcctca gggagcctct gccttaccca ctaccatcag cttcacttgc     240
tggaggcaac ccaatgaggg ttccagcagc caagaagagg aggggccaag cacctcgcct     300
gacgcagagt ccttgttccg agaagcactc agtaacaagg tggatgagtt ggctcatttt     360
ctgctccgca gtatcgagc caaggagctg gtcacaaagg cagaaatgct ggagagagtc     420
atcaaaaatt acaagcgctg ctttcctgtg atcttcggca agcctccga gtccctgaag     480 atgatctttg gcattgacgt gaaggaagtg gaccccacca gcaacaccta cacccttgtc     540
acctgcctgg gcctttccta tgatggcctg ctgggtaata atcagatctt cccaagaca     600 ggccttctga taatcgtcct gggcacaatt gcaatggagg cgacagcgc tctgaggag     660 gaaatctggg aggagctggg tgtgatgggg gtgtatgatg ggagggagca cactgtctat     720
ggggagccca ggaaactgct cacccaagat tgggtgcagg aaaactacct ggagtaccgg     780
caggtacccg gcagtaatcc tgcgcgctat gagttcctgt ggggtccaag ggctctggct     840
gaaaccagct atgtgaaagt cctggagcat gtggtcaggg tcaatgcaag agttcgcatt     900
```
gcctacccat ccctgcgtga agcagctttg ttagaggagg aagagggagt ctga    954

<210> SEQ ID NO 4
<211> LENGTH: 317
<212> TYPE: PRT
<213> ORGANISM: Homo sapiens

<400> SEQUENCE: 4

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Ser Pro Leu Val Pro
        35                  40                  45

Gly Thr Leu Glu Glu Val Pro Ala Ala Glu Ser Ala Gly Pro Pro Gln
    50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Gly Pro
                85                  90                  95

Ser Thr Ser Pro Asp Ala Glu Ser Leu Phe Arg Glu Ala Leu Ser Asn
            100                 105                 110

Lys Val Asp Glu Leu Ala His Phe Leu Leu Arg Lys Tyr Arg Ala Lys
        115                 120                 125

Glu Leu Val Thr Lys Ala Glu Met Leu Glu Arg Val Ile Lys Asn Tyr
    130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Thr Ser Asn Thr
                165                 170                 175

Tyr Thr Leu Val Thr Cys Leu Gly Leu Ser Tyr Asp Gly Leu Leu Gly
            180                 185                 190

Asn Asn Gln Ile Phe Pro Lys Thr Gly Leu Leu Ile Ile Val Leu Gly
        195                 200                 205

Thr Ile Ala Met Glu Gly Asp Ser Ala Ser Glu Glu Glu Ile Trp Glu
    210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Glu Asn Tyr
                245                 250                 255

Leu Glu Tyr Arg Gln Val Pro Gly Ser Asn Pro Ala Arg Tyr Glu Phe
            260                 265                 270

Leu Trp Gly Pro Arg Ala Leu Ala Glu Thr Ser Tyr Val Lys Val Leu
        275                 280                 285

Glu His Val Val Arg Val Asn Ala Arg Val Arg Ile Ala Tyr Pro Ser
    290                 295                 300

Leu Arg Glu Ala Ala Leu Leu Glu Glu Glu Gly Val
305                 310                 315

<210> SEQ ID NO 5
<211> LENGTH: 543
<212> TYPE: DNA
<213> ORGANISM: Homo sapiens

<400> SEQUENCE: 5

```
atgcaggccg aaggccgggg cacagggggt tcgacgggcg atgctgatgg cccaggaggc      60
cctggcattc ctgatggccc aggggcaat gctggcggcc caggagaggc gggtgccacg     120
ggcggcagag gtccccgggg cgcaggggca gcaagggcct cggggccggg aggaggcgcc     180
ccgcggggtc cgcatggcgg cgcggcttca gggctgaatg gatgctgcag atgcggggcc     240
agggggccgg agagccgcct gcttgagttc tacctcgcca tgcctttcgc gacacccatg     300
gaagcagagc tgcccgcag agcctggcc caggatgccc caccgcttcc cgtgccaggg      360
gtgcttctga aggagttcac tgtgtccggc aacatactga ctatccgact gactgctgca     420
gaccaccgcc aactgcagct ctccatcagc tcctgtctcc agcagctttc cctgttgatg     480
tggatcacgc agtgctttct gcccgtgttt ttggctcagc ctccctcagg gcagaggcgc     540
taa                                                                   543
```

<210> SEQ ID NO 6
<211> LENGTH: 180
<212> TYPE: PRT
<213> ORGANISM: Homo sapiens

<400> SEQUENCE: 6

```
Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180
```

<210> SEQ ID NO 7
<211> LENGTH: 246
<212> TYPE: DNA
<213> ORGANISM: Homo sapiens

<400> SEQUENCE: 7

```
atggagagcc ccaaaaagaa gaaccagcag ctgaaagtcg ggatcctaca cctgggcagc      60
agacagaaga agatcaggat acagctgaga tcccagtgcg cgacatggaa ggtgatctgc     120
aagagctgca tcagtcaaac accggggata aatctggatt tgggttccgg cgtcaaggtg     180
aagataatac ctaaagagga acactgtaaa atgccagaag caggtgaaga gcaaccacaa     240
``` gtttaa                                                                    246

<210> SEQ ID NO 8
<211> LENGTH: 81
<212> TYPE: PRT
<213> ORGANISM: Homo sapiens

<400> SEQUENCE: 8

Met Glu Ser Pro Lys Lys Asn Gln Gln Leu Lys Val Gly Ile Leu
1               5                   10                  15

His Leu Gly Ser Arg Gln Lys Lys Ile Arg Ile Gln Leu Arg Ser Gln
            20                  25                  30

Cys Ala Thr Trp Lys Val Ile Cys Lys Ser Cys Ile Ser Gln Thr Pro
        35                  40                  45

Gly Ile Asn Leu Asp Leu Gly Ser Gly Val Lys Val Lys Ile Ile Pro
    50                  55                  60

Lys Glu Glu His Cys Lys Met Pro Glu Ala Gly Glu Glu Gln Pro Gln
65                  70                  75                  80

Val

<210> SEQ ID NO 9
<211> LENGTH: 1698
<212> TYPE: DNA
<213> ORGANISM: Homo sapiens

<400> SEQUENCE: 9
atgaaagtac ccagaaacca ggactggctt ggtgtctcaa ggcaactcag aaccaaagcc      60
tggaacaggc agctgtatcc agagtggaca gaagcccaga gacttgactg ctggagaggt     120
ggtcaagtgt ccctcaaggt cagtaatgat gggcctacac tgattggtgc aaatgcctcc     180
ttctctattg ccttgaactt ccctggaagc caaaaggtat tgccagatgg caggttatc     240
tgggtcaaca ataccatcat caatgggagc caggtgtggg gaggacagcc agtgtatccc     300
caggaaactg acgatgcctg catcttccct gatggtggac cttgcccatc tggctcttgg     360
tctcagaaga gaagctttgt ttatgtctgg aagacctggg gccaatactg gcaagttcta     420
gggggcccag tgtctgggct gagcattggg acaggcaggg caatgctggg cacacacacc     480
atggaagtga ctgtctacca tcgccgggga tcccggagct atgtgcctct tgctcattcc     540
agctcagcct tcaccattac tgaccaggtg ccttttctccg tgagcgtgtc ccagttgcgg     600
gccttggatg gagggaacaa gcacttcctg agaaatcagc ctctgacctt tgccctccag     660
ctccatgacc ctagtggcta tctggctgaa gctgacctct cctacacctg gactttgga     720
gacagtagtg gaaccctgat ctctcgggca cttgtggtca ctcatactta cctggagcct     780
ggcccagtca ctgcccaggt ggtcctgcag gctgccattc tctcacctc tgtggctac     840
tccccagttc caggcaccac agatgggcac aggccaactg cagaggcccc taacaccaca     900
gctggccaag tgcctactac agaagttgtg ggtactacac tggtcaggc gccaactgca     960
gagccctctg aaccacatc tgtgcaggtg ccaaccactg aagtcataag cactgcacct    1020
gtgcagatgc caactgcaga gagcacaggt atgacctg agaaggtgcc agtttcagag    1080
gtcatgggta ccacactggc agagatgtca actccagagg ctacaggtat gacacctgca    1140
gaggtatcaa ttgtggtgct ttctggaacc acagctgcac aggtaacaac tacagagtgg    1200
gtggagacca cagctagaga gctacctatc cctgagcctg aaggtccaga tgccagctca    1260
atcatgtcta cggaaagtat tacaggttcc ctgggccccc tgctggatgg tacagccacc    1320

-continued

```
ttaaggctgg tgaagagaca agtcccctg gattgtgttc tgtatcgata tggttccttt    1380
tccgtcaccc tggacattgt ccagggtatt gaaagtgccg agatcctgca ggctgtgccg    1440
tccggtgagg gggatgcatt tgagctgact gtgtcctgcc aaggcgggct gcccaaggaa    1500
gcctgcatgg agatctcatc gccagggtgc cagcccctg cccagcggct gtgccagcct    1560
gtgctaccca gcccagcctg ccagctggtt ctgcaccaga tactgaaggg tggctcgggg    1620
acatactgcc tcaatgtgtc tctggctgat accaacagcc tggcagtggt cagcacccag    1680
cttatcatgc ctggttaa                                                  1698
```

<210> SEQ ID NO 10
<211> LENGTH: 565
<212> TYPE: PRT
<213> ORGANISM: Homo sapiens

<400> SEQUENCE: 10

```
Met Lys Val Pro Arg Asn Gln Asp Trp Leu Gly Val Ser Arg Gln Leu
1               5                   10                  15

Arg Thr Lys Ala Trp Asn Arg Gln Leu Tyr Pro Glu Trp Thr Glu Ala
            20                  25                  30

Gln Arg Leu Asp Cys Trp Arg Gly Gln Val Ser Leu Lys Val Ser
        35                  40                  45

Asn Asp Gly Pro Thr Leu Ile Gly Ala Asn Ala Ser Phe Ser Ile Ala
50                  55                  60

Leu Asn Phe Pro Gly Ser Gln Lys Val Leu Pro Asp Gly Gln Val Ile
65                  70                  75                  80

Trp Val Asn Asn Thr Ile Ile Asn Gly Ser Gln Val Trp Gly Gly Gln
                85                  90                  95

Pro Val Tyr Pro Gln Glu Thr Asp Asp Ala Cys Ile Phe Pro Asp Gly
            100                 105                 110

Gly Pro Cys Pro Ser Gly Ser Trp Ser Gln Lys Arg Ser Phe Val Tyr
        115                 120                 125

Val Trp Lys Thr Trp Gly Gln Tyr Trp Gln Val Leu Gly Gly Pro Val
130                 135                 140

Ser Gly Leu Ser Ile Gly Thr Gly Arg Ala Met Leu Gly Thr His Thr
145                 150                 155                 160

Met Glu Val Thr Val Tyr His Arg Arg Gly Ser Arg Ser Tyr Val Pro
                165                 170                 175

Leu Ala His Ser Ser Ser Ala Phe Thr Ile Thr Asp Gln Val Pro Phe
            180                 185                 190

Ser Val Ser Val Ser Gln Leu Arg Ala Leu Asp Gly Gly Asn Lys His
        195                 200                 205

Phe Leu Arg Asn Gln Pro Leu Thr Phe Ala Leu Gln Leu His Asp Pro
210                 215                 220

Ser Gly Tyr Leu Ala Glu Ala Asp Leu Ser Tyr Thr Trp Asp Phe Gly
225                 230                 235                 240

Asp Ser Ser Gly Thr Leu Ile Ser Arg Ala Leu Val Val Thr His Thr
                245                 250                 255

Tyr Leu Glu Pro Gly Pro Val Thr Ala Gln Val Val Leu Gln Ala Ala
            260                 265                 270

Ile Pro Leu Thr Ser Cys Gly Tyr Ser Pro Val Pro Gly Thr Thr Asp
        275                 280                 285

Gly His Arg Pro Thr Ala Glu Ala Pro Asn Thr Thr Ala Gly Gln Val
290                 295                 300
```

```
Pro Thr Thr Glu Val Val Gly Thr Thr Pro Gly Gln Ala Pro Thr Ala
305                 310                 315                 320

Glu Pro Ser Gly Thr Thr Ser Val Gln Val Pro Thr Thr Glu Val Ile
            325                 330                 335

Ser Thr Ala Pro Val Gln Met Pro Thr Ala Glu Ser Thr Gly Met Thr
            340                 345                 350

Pro Glu Lys Val Pro Val Ser Glu Val Met Gly Thr Thr Leu Ala Glu
            355                 360                 365

Met Ser Thr Pro Glu Ala Thr Gly Met Thr Pro Ala Glu Val Ser Ile
370                 375                 380

Val Val Leu Ser Gly Thr Thr Ala Ala Gln Val Thr Thr Thr Glu Trp
385                 390                 395                 400

Val Glu Thr Thr Ala Arg Glu Leu Pro Ile Pro Glu Pro Glu Gly Pro
                405                 410                 415

Asp Ala Ser Ser Ile Met Ser Thr Glu Ser Ile Thr Gly Ser Leu Gly
                420                 425                 430

Pro Leu Leu Asp Gly Thr Ala Thr Leu Arg Leu Val Lys Arg Gln Val
            435                 440                 445

Pro Leu Asp Cys Val Leu Tyr Arg Tyr Gly Ser Phe Ser Val Thr Leu
            450                 455                 460

Asp Ile Val Gln Gly Ile Glu Ser Ala Glu Ile Leu Gln Ala Val Pro
465                 470                 475                 480

Ser Gly Glu Gly Asp Ala Phe Glu Leu Thr Val Ser Cys Gln Gly Gly
                485                 490                 495

Leu Pro Lys Glu Ala Cys Met Glu Ile Ser Ser Pro Gly Cys Gln Pro
            500                 505                 510

Pro Ala Gln Arg Leu Cys Gln Pro Val Leu Pro Ser Pro Ala Cys Gln
            515                 520                 525

Leu Val Leu His Gln Ile Leu Lys Gly Gly Ser Gly Thr Tyr Cys Leu
            530                 535                 540

Asn Val Ser Leu Ala Asp Thr Asn Ser Leu Ala Val Val Ser Thr Gln
545                 550                 555                 560

Leu Ile Met Pro Gly
                565
```

<210> SEQ ID NO 11
<211> LENGTH: 429
<212> TYPE: DNA
<213> ORGANISM: Homo sapiens

<400> SEQUENCE: 11

```
atgggtgccc cgacgttgcc ccctgcctgg cagcccttc  tcaaggacca ccgcatctct    60
acattcaaga actggccctt cttggagggc tgcgcctgca ccccggagcg gatggccgag   120
gctggcttca tccactgccc cactgagaac gagccagact tggcccagtg tttcttctgc   180
ttcaaggagc tggaaggctg ggagccagat gacgaccca  tagaggaaca taaaaagcat   240
tcgtccggtt gcgcttttcct ttctgtcaag aagcagtttg aagaattaac ccttggtgaa   300
tttttgaaac tggacagaga aagagccaag aacaaaattg caaaggaaac caacaataag   360
aagaaagaat ttgaggaaac tgcggagaaa gtgcgccgtg ccatcgagca gctggctgcc   420
atggattga                                                          429
```

<210> SEQ ID NO 12
<211> LENGTH: 142

```
<212> TYPE: PRT
<213> ORGANISM: Homo sapiens

<400> SEQUENCE: 12

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His
65                  70                  75                  80

Ser Ser Gly Cys Ala Phe Leu Ser Val Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Glu Lys Val Arg Arg Ala Ile Glu Gln Leu Ala Ala Met Asp
    130                 135                 140

<210> SEQ ID NO 13
<211> LENGTH: 129
<212> TYPE: PRT
<213> ORGANISM: Gallus gallus

<400> SEQUENCE: 13

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
            20                  25                  30

Lys Phe Glu Ser Asn Phe Asn Thr Gln Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu

<210> SEQ ID NO 14
<211> LENGTH: 1618
<212> TYPE: DNA
<213> ORGANISM: Artificial
<220> FEATURE:
<223> OTHER INFORMATION: His-tag fusion protein

<400> SEQUENCE: 14
atgggcagca gccatcatca tcatcatcac agcagcggcc tggtgccgcg cggcagccat      60
atgcaggacc cggcttccac cgtgtgtccg gagccggcgt ctcagcacac gctccgctcc     120
```

```
gggcctgggt gcctacagca gccagagcag cagggagtcc gggacccggg cggcatctgg      180
gccaagttag gcgccgccga ggccagcgct aacgtctcc agggccggag gagccgcggg       240
gcgtccgggt ctgagccgca gcaaatgggc tccgacgtgc gggacctgaa cgcgctgctg      300
cccgccgtcc cctccctggg tggcggcggc ggctgtgccc tgcctgtgag cggcgcggcg      360
cagtgggcgc cggtgctgga ctttgcgccc ccgggcgctt cggcttacgg gtcgttgggc      420
ggccccgcgc cgccaccggc tccgccgcca ccccgccgc cgccgcctca ctccttcatc       480
aaacaggagc cgagctgggg cggcgcggag ccgcacgagg agcagtgcct gagcgccttc      540
actgtccact tttccggcca gttcactggc acagccggag cctgtcgcta cgggcccttc      600
ggtcctcctc cgcccagcca ggcgtcatcc ggccaggcca ggatgttttcc taacgcgccc     660 tacctgccca gctgcctcga gagccagccc gctattcgca atcagggtta cagcacggtc      720
accttcgacg ggacgcccag ctacggtcac acgccctcgc accatgcggc gcagttcccc      780
aaccactcat tcaagcatga ggatcccatg ggccagcagg gctcgctggg tgagcagcag      840
tactcggtgc cgcccccggt ctatggctgc cacaccccca ccgacagctg caccggcagc      900 caggcttttgc tgctgaggac gccctacagc agtgacaatt tataccaaat gacatcccag     960
cttgaatgca tgacctggaa tcagatgaac ttaggagcca ccttaaaggg agttgctgct      1020
gggagctcca gctcagtgaa atggacagaa gggcagagca accacagcac agggtacgag     1080
agcgataacc acacaacgcc catcctctgc ggagcccaat acagaataca cacgcacggt      1140
gtcttcagag gcattcagga tgtgcgacgt gtgcctggag tagcccccgac tcttgtacgg     1200 tcggcatctg agaccagtga gaaacgcccc ttcatgtgtg cttacccagg ctgcaataag      1260
agatatttta gctgtcccca cttacagatg cacagcagga agcacactgg tgagaaacca      1320
taccagtgtg acttcaagga ctgtgaacga aggttttctc gttcagacca gctcaaaaga      1380
caccaaagga gacatacagg tgtgaaacca ttccagtgta aaacttgtca gcgaaagttc      1440
tcccggtccg accacctgaa gacccacacc aggactcata caggtaaaac aagtgaaaag      1500
cccttcagct gtcggtggcc aagttgtcag aaaaagtttg cccggtcaga tgaattagtc      1560
cgccatcaca acatgcatca gagaaacatg accaaactcc agctggcgct ttgaattc        1618
```

<210> SEQ ID NO 15
<211> LENGTH: 537
<212> TYPE: PRT
<213> ORGANISM: Artificial
<220> FEATURE:
<223> OTHER INFORMATION: His-tag fusion protein

<400> SEQUENCE: 15

```
Met Gly Ser Ser His His His His His His Ser Ser Gly Leu Val Pro
1               5                   10                  15

Arg Gly Ser His Met Gln Asp Pro Ala Ser Thr Cys Val Pro Glu Pro
            20                  25                  30

Ala Ser Gln His Thr Leu Arg Ser Gly Pro Gly Cys Leu Gln Gln Pro
        35                  40                  45

Glu Gln Gln Gly Val Arg Asp Pro Gly Gly Ile Trp Ala Lys Leu Gly
    50                  55                  60

Ala Ala Glu Ala Ser Ala Glu Arg Leu Gln Gly Arg Arg Ser Arg Gly
65                  70                  75                  80

Ala Ser Gly Ser Glu Pro Gln Gln Met Gly Ser Asp Val Arg Asp Leu
                85                  90                  95
```

```
Asn Ala Leu Leu Pro Ala Val Pro Ser Leu Gly Gly Gly Gly Cys
            100                 105                 110

Ala Leu Pro Val Ser Gly Ala Ala Gln Trp Ala Pro Val Leu Asp Phe
        115                 120                 125

Ala Pro Pro Gly Ala Ser Ala Tyr Gly Ser Leu Gly Gly Pro Ala Pro
    130                 135                 140

Pro Pro Ala Pro Pro Pro Pro Pro Pro Pro His Ser Phe Ile
145                 150                 155                 160

Lys Gln Glu Pro Ser Trp Gly Gly Ala Glu Pro His Glu Glu Gln Cys
                165                 170                 175

Leu Ser Ala Phe Thr Val His Phe Ser Gly Gln Phe Thr Gly Thr Ala
            180                 185                 190

Gly Ala Cys Arg Tyr Gly Pro Phe Gly Pro Pro Pro Ser Gln Ala
        195                 200                 205

Ser Ser Gly Gln Ala Arg Met Phe Pro Asn Ala Pro Tyr Leu Pro Ser
    210                 215                 220

Cys Leu Glu Ser Gln Pro Ala Ile Arg Asn Gln Gly Tyr Ser Thr Val
225                 230                 235                 240

Thr Phe Asp Gly Thr Pro Ser Tyr Gly His Thr Pro Ser His His Ala
                245                 250                 255

Ala Gln Phe Pro Asn His Ser Phe Lys His Glu Asp Pro Met Gly Gln
            260                 265                 270

Gln Gly Ser Leu Gly Glu Gln Gln Tyr Ser Val Pro Pro Val Tyr
        275                 280                 285

Gly Cys His Thr Pro Thr Asp Ser Cys Thr Gly Ser Gln Ala Leu Leu
    290                 295                 300

Leu Arg Thr Pro Tyr Ser Ser Asp Asn Leu Tyr Gln Met Thr Ser Gln
305                 310                 315                 320

Leu Glu Cys Met Thr Trp Asn Gln Met Asn Leu Gly Ala Thr Leu Lys
                325                 330                 335

Gly Val Ala Ala Gly Ser Ser Ser Val Lys Trp Thr Glu Gly Gln
        340                 345                 350

Ser Asn His Ser Thr Gly Tyr Glu Ser Asp Asn His Thr Thr Pro Ile
    355                 360                 365

Leu Cys Gly Ala Gln Tyr Arg Ile His Thr His Gly Val Phe Arg Gly
370                 375                 380

Ile Gln Asp Val Arg Arg Val Pro Gly Val Ala Pro Thr Leu Val Arg
385                 390                 395                 400

Ser Ala Ser Glu Thr Ser Glu Lys Arg Pro Phe Met Cys Ala Tyr Pro
                405                 410                 415

Gly Cys Asn Lys Arg Tyr Phe Lys Leu Ser His Leu Gln Met His Ser
            420                 425                 430

Arg Lys His Thr Gly Glu Lys Pro Tyr Gln Cys Asp Phe Lys Asp Cys
        435                 440                 445

Glu Arg Arg Phe Ser Arg Ser Asp Gln Leu Lys Arg His Gln Arg Arg
    450                 455                 460

His Thr Gly Val Lys Pro Phe Gln Cys Lys Thr Cys Gln Arg Lys Phe
465                 470                 475                 480

Ser Arg Ser Asp His Leu Lys Thr His Thr Arg Thr His Thr Gly Lys
                485                 490                 495

Thr Ser Glu Lys Pro Phe Ser Cys Arg Trp Pro Ser Cys Gln Lys Lys
            500                 505                 510

Phe Ala Arg Ser Asp Glu Leu Val Arg His His Asn Met His Gln Arg
```

```
            515                 520                 525

Asn Met Thr Lys Leu Gln Leu Ala Leu
    530                 535

<210> SEQ ID NO 16
<211> LENGTH: 1020
<212> TYPE: DNA
<213> ORGANISM: Artificial
<220> FEATURE:
<223> OTHER INFORMATION: His-tag fusion protein

<400> SEQUENCE: 16
atgggcagca gccatcatca tcatcatcac agcagcggcc tggtgccgcg cggcagccat      60
atgtcttctg agcagaagag tcagcactgc aagcctgagg aaggcgttga ggcccaagaa     120
gaggccctgg gctggtgggt gcgcaggct cctactactg aggagcagga ggctgctgtc     180
tcctcctcct ctcctctggt ccctggcacc ctggaggaag tgcctgctgc tgagtcagca     240
ggtcctcccc agagtcctca gggagcctct gccttaccca ctaccatcag cttcacttgc     300
tggaggcaac ccaatgaggg ttccagcagc caagaagagg aggggccaag cacctcgcct     360
gacgcagagt ccttgttccg agaagcactc agtaacaagg tggatgagtt ggctcatttt     420
ctgctccgca gtatcgagc caaggagctg gtcacaaagg cagaaatgct ggagagagtc     480
atcaaaaatt acaagcgctg ctttcctgtg atcttcggca agcctccga gtccctgaag     540 atgatctttg gcattgacgt gaaggaagtg gaccccacca gcaacaccta caccttgtc     600 acctgcctgg ccttttccta tgatggcctg ctgggtaata atcagatctt tcccaagaca     660
ggccttctga taatcgtcct gggcacaatt gcaatggagg gcgacagcgc tctgaggag     720 gaaatctggg aggagctggg tgtgatgggg gtgtatgatg ggagggagca cactgtctat     780
ggggagccca ggaaactgct cacccaagat tgggtgcagg aaaactacct ggagtaccgg     840
caggtacccg gcagtaatcc tgcgcgctat gagttcctgt ggggtccaag ggctctggct     900
gaaaccagct atgtgaaagt cctggagcat gtggtcaggg tcaatgcaag agttcgcatt     960
gcctacccat ccctgcgtga agcagctttg ttagaggagg aagagggagt ctgaggatcc    1020

<210> SEQ ID NO 17
<211> LENGTH: 337
<212> TYPE: PRT
<213> ORGANISM: Artificial
<220> FEATURE:
<223> OTHER INFORMATION: His-tag fusion protein

<400> SEQUENCE: 17

Met Gly Ser Ser His His His His His His Ser Ser Gly Leu Val Pro
1               5                   10                  15

Arg Gly Ser His Met Ser Ser Glu Gln Lys Ser Gln His Cys Lys Pro
            20                  25                  30

Glu Glu Gly Val Glu Ala Gln Glu Glu Ala Leu Gly Leu Val Gly Ala
        35                  40                  45

Gln Ala Pro Thr Thr Glu Glu Gln Glu Ala Ala Val Ser Ser Ser Ser
    50                  55                  60

Pro Leu Val Pro Gly Thr Leu Glu Glu Val Pro Ala Ala Glu Ser Ala
65                  70                  75                  80

Gly Pro Pro Gln Ser Pro Gln Gly Ala Ser Ala Leu Pro Thr Thr Ile
                85                  90                  95

Ser Phe Thr Cys Trp Arg Gln Pro Asn Glu Gly Ser Ser Ser Gln Glu
            100                 105                 110
```

```
Glu Glu Gly Pro Ser Thr Ser Pro Asp Ala Glu Ser Leu Phe Arg Glu
            115                 120                 125

Ala Leu Ser Asn Lys Val Asp Glu Leu Ala His Phe Leu Leu Arg Lys
        130                 135                 140

Tyr Arg Ala Lys Glu Leu Val Thr Lys Ala Glu Met Leu Glu Arg Val
145                 150                 155                 160

Ile Lys Asn Tyr Lys Arg Cys Phe Pro Val Ile Phe Gly Lys Ala Ser
                165                 170                 175

Glu Ser Leu Lys Met Ile Phe Gly Ile Asp Val Lys Glu Val Asp Pro
            180                 185                 190

Thr Ser Asn Thr Tyr Thr Leu Val Thr Cys Leu Gly Leu Ser Tyr Asp
        195                 200                 205

Gly Leu Leu Gly Asn Asn Gln Ile Phe Pro Lys Thr Gly Leu Leu Ile
210                 215                 220

Ile Val Leu Gly Thr Ile Ala Met Glu Gly Asp Ser Ala Ser Glu Glu
225                 230                 235                 240

Glu Ile Trp Glu Glu Leu Gly Val Met Gly Val Tyr Asp Gly Arg Glu
                245                 250                 255

His Thr Val Tyr Gly Glu Pro Arg Lys Leu Leu Thr Gln Asp Trp Val
            260                 265                 270

Gln Glu Asn Tyr Leu Glu Tyr Arg Gln Val Pro Gly Ser Asn Pro Ala
        275                 280                 285

Arg Tyr Glu Phe Leu Trp Gly Pro Arg Ala Leu Ala Glu Thr Ser Tyr
    290                 295                 300

Val Lys Val Leu Glu His Val Arg Val Asn Ala Arg Val Arg Ile
305                 310                 315                 320

Ala Tyr Pro Ser Leu Arg Glu Ala Ala Leu Leu Glu Glu Glu Gly
                325                 330                 335

Val

<210> SEQ ID NO 18
<211> LENGTH: 735
<212> TYPE: DNA
<213> ORGANISM: Artificial
<220> FEATURE:
<223> OTHER INFORMATION: His-tag fusion protein

<400> SEQUENCE: 18
atgggcagca gccatcatca tcatcatcac agcagcggcc tggtgccgcg cggcagccat      60
atggctagca tgactggtgg acagcaaatg ggtcgcggat ccatgcaggc cgaaggccgg     120
ggcacagggg gttcgacggg cgatgctgat ggcccaggag ccctggcat tcctgatggc     180 ccagggggca atgctggcgg cccaggagag gcgggtgcca cgggcggcag aggtccccgg     240
ggcgcagggg cagcaagggc ctcggggccg ggaggaggcg ccccgcgggg tccgcatggc     300
ggcgcggctt cagggctgaa tgatgctgc agatgcgggg ccaggggcc ggagagccgc      360 ctgcttgagt tctacctcgc catgcctttc gcgacaccca tggaagcaga gctggcccgc      420
aggagcctgg cccaggatgc cccaccgctt cccgtgccag gggtgcttct gaaggagttc      480
actgtgtccg gcaacatact gactatccga ctgactgctg cagaccaccg ccaactgcag      540
ctctccatca gctcctgtct ccagcagctt ccctgttga tgtggatcac gcagtgcttt      600
ctgcccgtgt ttttggctca gcctcccctca gggcagaggc gctaacagct ttccctgttg      660
atgtggatca cgcagtgctt tctgcccgtg ttttggctca gcctcccctc agggcagagg     720
```

```
cgctaagcca agctt                                                    735
```

```
<210> SEQ ID NO 19
<211> LENGTH: 214
<212> TYPE: PRT
<213> ORGANISM: Artificial
<220> FEATURE:
<223> OTHER INFORMATION: His-tag fusion protein

<400> SEQUENCE: 19
```

Met Gly Ser Ser His His His His His Ser Ser Gly Leu Val Pro
1               5                  10                  15

Arg Gly Ser His Met Ala Ser Met Thr Gly Gly Gln Gln Met Gly Arg
            20                  25                  30

Gly Ser Met Gln Ala Glu Gly Arg Gly Thr Gly Gly Ser Thr Gly Asp
        35                  40                  45

Ala Asp Gly Pro Gly Gly Pro Gly Ile Pro Asp Gly Pro Gly Gly Asn
    50                  55                  60

Ala Gly Gly Pro Gly Glu Ala Gly Ala Thr Gly Gly Arg Gly Pro Arg
65                  70                  75                  80

Gly Ala Gly Ala Ala Arg Ala Ser Gly Pro Gly Gly Gly Ala Pro Arg
                85                  90                  95

Gly Pro His Gly Gly Ala Ala Ser Gly Leu Asn Gly Cys Cys Arg Cys
            100                 105                 110

Gly Ala Arg Gly Pro Glu Ser Arg Leu Leu Glu Phe Tyr Leu Ala Met
        115                 120                 125

Pro Phe Ala Thr Pro Met Glu Ala Glu Leu Ala Arg Arg Ser Leu Ala
    130                 135                 140

Gln Asp Ala Pro Pro Leu Pro Val Pro Gly Val Leu Leu Lys Glu Phe
145                 150                 155                 160

Thr Val Ser Gly Asn Ile Leu Thr Ile Arg Leu Thr Ala Ala Asp His
                165                 170                 175

Arg Gln Leu Gln Leu Ser Ile Ser Ser Cys Leu Gln Gln Leu Ser Leu
            180                 185                 190

Leu Met Trp Ile Thr Gln Cys Phe Leu Pro Val Phe Leu Ala Gln Pro
        195                 200                 205

Pro Ser Gly Gln Arg Arg
    210

```
<210> SEQ ID NO 20
<211> LENGTH: 377
<212> TYPE: DNA
<213> ORGANISM: Artificial
<220> FEATURE:
<223> OTHER INFORMATION: His-tag fusion protein

<400> SEQUENCE: 20
atgggcagca gccatcatca tcatcatcac agcagcggcc tggtgccgcg cggcagccat    60
atggctagca tgactggtgg acagcaaatg ggtcgcggat ccgaattccg catggagagc   120
cccaaaaaga agaaccagca gctgaaagtc gggatcctac acctgggcag cagacagaag   180
aagatcagga tacagctgag atcccagtgc gcgacatgga aggtgatctg caagagctgc   240
atcagtcaaa caccggggat aaatctggat ttgggttccg gcgtcaaggt gaagataata   300 cctaagagg aacactgtaa aatgccagaa gcaggtgaag agcaaccaca agtttaaatg   360
aagacaagct gctcgag                                                  377
```

```
<210> SEQ ID NO 21
<211> LENGTH: 118
<212> TYPE: PRT
<213> ORGANISM: Artificial
<220> FEATURE:
<223> OTHER INFORMATION: His-tag fusion protein

<400> SEQUENCE: 21

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Arg Met Glu Ser Pro Lys Lys Lys Asn Gln Gln Leu
        35                  40                  45

Lys Val Gly Ile Leu His Leu Gly Ser Arg Gln Lys Lys Ile Arg Ile
    50                  55                  60

Gln Leu Arg Ser Gln Cys Ala Thr Trp Lys Val Ile Cys Lys Ser Cys
65                  70                  75                  80

Ile Ser Gln Thr Pro Gly Ile Asn Leu Asp Leu Gly Ser Gly Val Lys
                85                  90                  95

Val Lys Ile Ile Pro Lys Glu Glu His Cys Lys Met Pro Glu Ala Gly
            100                 105                 110

Glu Glu Gln Pro Gln Val
        115

<210> SEQ ID NO 22
<211> LENGTH: 1766
<212> TYPE: DNA
<213> ORGANISM: Artificial
<220> FEATURE:
<223> OTHER INFORMATION: His-tag fusion protein

<400> SEQUENCE: 22
atgggcagca gccatcatca tcatcatcac agcagcggcc tggtgccgcg cggcagccat      60
atgaaagtac ccagaaacca ggactggctt ggtgtctcaa ggcaactcag aaccaaagcc     120
tggaacaggc agctgtatcc agagtggaca gaagcccaga gacttgactg ctggagaggt     180
ggtcaagtgt ccctcaaggt cagtaatgat gggcctacac tgattggtgc aaatgcctcc     240
ttctctattg ccttgaactt ccctggaagc caaaaggtat gccagatggg caggttatc      300 tgggtcaaca taccatcat caatgggagc caggtgtggg aggacagcc agtgtatccc       360 caggaaactg acgatgcctg catcttccct gatggtggac cttgcccatc tggctcttgg     420
tctcagaaga gaagctttgt ttatgtctgg aagacctggg ccaatactg gcaagttcta     480 gggggcccag tgtctgggct gagcattggg acaggcaggg caatgctggg cacacacacc     540
atggaagtga ctgtctacca tcgccgggga tcccggagct atgtgcctct tgctcattcc     600
agctcagcct tcaccattac tgaccaggtg cctttctccg tgagcgtgtc ccagttgcgg     660
gccttggatg agggaacaa gcacttcctg agaaatcagc tctgaccttt gccctccag      720 ctccatgacc ctagtggcta tctggctgaa gctgacctct cctacacctg gactttgga     780 gacagtagtg gaaccctgat ctctcgggca cttgtggtca ctcatactta cctggagcct     840
ggcccagtca ctgcccaggt ggtcctgcag gctgccattc ctctcacctc ctgtggctac     900 tcccagttc aggcaccac agatgggcac aggccaactg cagaggcccc taacaccaca     960
gctggccaag tgcctactac agaagttgtg ggtactacac tggtcaggc gccaactgca    1020 gagccctctg gaaccacatc tgtgcaggtg ccaaccactaa agtcataag cactgcacct    1080
```

-continued

```
gtgcagatgc caactgcaga gagcacaggt atgacacctg agaaggtgcc agtttcagag    1140
gtcatgggta ccacactggc agagatgtca actccagagg ctacaggtat gacacctgca    1200
gaggtatcaa ttgtggtgct ttctggaacc acagctgcac aggtaacaac tacagagtgg    1260
gtggagacca cagctagaga gctacctatc cctgagcctg aaggtccaga tgccagctca    1320
atcatgtcta cggaaagtat tacaggttcc ctgggccccc tgctggatgg tacagccacc    1380
ttaaggctgg tgaagagaca agtccccctg gattgtgttc tgtatcgata tggttccttt    1440
tccgtcaccc tggacattgt ccagggtatt gaaagtgccg agatcctgca ggctgtgccg    1500
tccggtgagg gggatgcatt tgagctgact gtgtcctgcc aaggcgggct gcccaaggaa    1560
gcctgcatgg agatctcatc gccagggtgc cagcccctg cccagcggct gtgccagcct    1620
gtgctaccca gcccagcctg ccagctggtt ctgcaccaga tactgaaggg tggctcgggg    1680
acatactgcc tcaatgtgtc tctggctgat accaacagcc tggcagtggt cagcacccag    1740
cttatcatgc tggttaagc ggccgc                                          1766
```

<210> SEQ ID NO 23
<211> LENGTH: 585
<212> TYPE: PRT
<213> ORGANISM: Artificial
<220> FEATURE:
<223> OTHER INFORMATION: His-tag fusion protein

<400> SEQUENCE: 23

```
Met Gly Ser Ser His His His His His His Ser Ser Gly Leu Val Pro
1               5                   10                  15

Arg Gly Ser His Met Lys Val Pro Arg Asn Gln Asp Trp Leu Gly Val
                20                  25                  30

Ser Arg Gln Leu Arg Thr Lys Ala Trp Asn Arg Gln Leu Tyr Pro Glu
            35                  40                  45

Trp Thr Glu Ala Gln Arg Leu Asp Cys Trp Arg Gly Gly Gln Val Ser
        50                  55                  60

Leu Lys Val Ser Asn Asp Gly Pro Thr Leu Ile Gly Ala Asn Ala Ser
65                  70                  75                  80

Phe Ser Ile Ala Leu Asn Phe Pro Gly Ser Gln Lys Val Leu Pro Asp
                85                  90                  95

Gly Gln Val Ile Trp Val Asn Asn Thr Ile Ile Asn Gly Ser Gln Val
            100                 105                 110

Trp Gly Gly Gln Pro Val Tyr Pro Gln Glu Thr Asp Asp Ala Cys Ile
        115                 120                 125

Phe Pro Asp Gly Gly Pro Cys Pro Ser Gly Ser Trp Ser Gln Lys Arg
    130                 135                 140

Ser Phe Val Tyr Val Trp Lys Thr Trp Gly Gln Tyr Trp Gln Val Leu
145                 150                 155                 160

Gly Gly Pro Val Ser Gly Leu Ser Ile Gly Thr Gly Arg Ala Met Leu
                165                 170                 175

Gly Thr His Thr Met Glu Val Thr Val Tyr His Arg Arg Gly Ser Arg
            180                 185                 190

Ser Tyr Val Pro Leu Ala His Ser Ser Ala Phe Thr Ile Thr Asp
        195                 200                 205

Gln Val Pro Phe Ser Val Ser Val Ser Gln Leu Arg Ala Leu Asp Gly
    210                 215                 220

Gly Asn Lys His Phe Leu Arg Asn Gln Pro Leu Thr Phe Ala Leu Gln
225                 230                 235                 240
```

```
Leu His Asp Pro Ser Gly Tyr Leu Ala Glu Ala Asp Leu Ser Tyr Thr
                245                 250                 255

Trp Asp Phe Gly Asp Ser Ser Gly Thr Leu Ile Ser Arg Ala Leu Val
            260                 265                 270

Val Thr His Thr Tyr Leu Glu Pro Gly Pro Val Thr Ala Gln Val Val
        275                 280                 285

Leu Gln Ala Ala Ile Pro Leu Thr Ser Cys Gly Tyr Ser Pro Val Pro
    290                 295                 300

Gly Thr Thr Asp Gly His Arg Pro Thr Ala Glu Ala Pro Asn Thr Thr
305                 310                 315                 320

Ala Gly Gln Val Pro Thr Thr Glu Val Val Gly Thr Thr Pro Gly Gln
                325                 330                 335

Ala Pro Thr Ala Glu Pro Ser Gly Thr Thr Ser Val Gln Val Pro Thr
            340                 345                 350

Thr Glu Val Ile Ser Thr Ala Pro Val Gln Met Pro Thr Ala Glu Ser
        355                 360                 365

Thr Gly Met Thr Pro Glu Lys Val Pro Val Ser Glu Val Met Gly Thr
    370                 375                 380

Thr Leu Ala Glu Met Ser Thr Pro Glu Ala Thr Gly Met Thr Pro Ala
385                 390                 395                 400

Glu Val Ser Ile Val Val Leu Ser Gly Thr Thr Ala Ala Gln Val Thr
                405                 410                 415

Thr Thr Glu Trp Val Glu Thr Thr Ala Arg Glu Leu Pro Ile Pro Glu
            420                 425                 430

Pro Glu Gly Pro Asp Ala Ser Ser Ile Met Ser Thr Glu Ser Ile Thr
        435                 440                 445

Gly Ser Leu Gly Pro Leu Leu Asp Gly Thr Ala Thr Leu Arg Leu Val
    450                 455                 460

Lys Arg Gln Val Pro Leu Asp Cys Val Leu Tyr Arg Tyr Gly Ser Phe
465                 470                 475                 480

Ser Val Thr Leu Asp Ile Val Gln Gly Ile Glu Ser Ala Glu Ile Leu
                485                 490                 495

Gln Ala Val Pro Ser Gly Glu Gly Asp Ala Phe Glu Leu Thr Val Ser
            500                 505                 510

Cys Gln Gly Gly Leu Pro Lys Glu Ala Cys Met Glu Ile Ser Ser Pro
        515                 520                 525

Gly Cys Gln Pro Pro Ala Gln Arg Leu Cys Gln Pro Val Leu Pro Ser
    530                 535                 540

Pro Ala Cys Gln Leu Val Leu His Gln Ile Leu Lys Gly Gly Ser Gly
545                 550                 555                 560

Thr Tyr Cys Leu Asn Val Ser Leu Ala Asp Thr Asn Ser Leu Ala Val
                565                 570                 575

Val Ser Thr Gln Leu Ile Met Pro Gly
            580                 585

<210> SEQ ID NO 24
<211> LENGTH: 537
<212> TYPE: DNA
<213> ORGANISM: Artificial
<220> FEATURE:
<223> OTHER INFORMATION: His-tag fusion protein

<400> SEQUENCE: 24
atgggcagca gccatcatca tcatcatcac agcagcggcc tggtgccgcg cggcagccat      60
atggctagca tgactggtgg acagcaaatg ggtcgcggat ccatgggtgc cccgacgttg     120
```

```
ccccctgcct ggcagccctt tctcaaggac caccgcatct ctacattcaa gaactggccc    180
ttcttggagg gctgcgcctg cacccggag cggatggccg aggctggctt catccactgc    240
cccactgaga acgagccaga cttggcccag tgtttcttct gcttcaagga gctggaaggc    300
tgggagccag atgacgaccc catagaggaa cataaaaagc attcgtccgg ttgcgctttc    360
ctttctgtca agaagcagtt tgaagaatta acccttggtg aatttttgaa actggacaga    420
gaaagagcca agaacaaaat tgcaaaggaa accaacaata agaagaaaga atttgaggaa    480
actgcggaga aagtgcgccg tgccatcgag cagctggctg ccatggattg actcgag      537

<210> SEQ ID NO 25
<211> LENGTH: 176
<212> TYPE: PRT
<213> ORGANISM: Artificial
<220> FEATURE:
<223> OTHER INFORMATION: His-tag fusion protein

<400> SEQUENCE: 25

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Met Gly Ala Pro Thr Leu Pro Pro Ala Trp Gln Pro Phe Leu
        35                  40                  45

Lys Asp His Arg Ile Ser Thr Phe Lys Asn Trp Pro Phe Leu Glu Gly
    50                  55                  60

Cys Ala Cys Thr Pro Glu Arg Met Ala Glu Ala Gly Phe Ile His Cys
65                  70                  75                  80

Pro Thr Glu Asn Glu Pro Asp Leu Ala Gln Cys Phe Phe Cys Phe Lys
                85                  90                  95

Glu Leu Glu Gly Trp Glu Pro Asp Asp Asp Pro Ile Glu Glu His Lys
            100                 105                 110

Lys His Ser Ser Gly Cys Ala Phe Leu Ser Val Lys Lys Gln Phe Glu
        115                 120                 125

Glu Leu Thr Leu Gly Glu Phe Leu Lys Leu Asp Arg Glu Arg Ala Lys
    130                 135                 140

Asn Lys Ile Ala Lys Glu Thr Asn Asn Lys Lys Lys Glu Phe Glu Glu
145                 150                 155                 160

Thr Ala Glu Lys Val Arg Arg Ala Ile Glu Gln Leu Ala Ala Met Asp
                165                 170                 175
```

METHOD FOR PRODUCING REAGENT FOR ANTIBODY DETECTION AND USE THEREOF

TECHNICAL FIELD

The present invention relates to a method for producing a reagent for antibody detection. The present invention also relates to a reagent for antibody detection produced by the method and use thereof.

BACKGROUND ART

There exist a large number of methods for detecting antibodies contained in liquid samples, for example, radioimmunoassay and enzyme-linked immunosorbent assay (ELISA). ELISA is a method which involves: immobilizing particular antigens onto a microplate; after serial dilution of an antibody-containing sample, performing antigen-antibody reaction on the microplate; and detecting the bound antibody using an enzyme-labeled secondary antibody. This method requires evaluating antibody tests directed to individual antigens using separate assay plates.

As an approach for solving this problem, a multiplex technique has received attention, which can simultaneously analyze antibodies against diverse antigens by use of microbeads bearing reporter fluorescence as a carrier for immobilization.

In the application of any of these techniques, such diverse antigens must be prepared in water-soluble forms. Proteins of native structures that can be prepared in water-soluble forms or chemically synthesized polypeptide fragments have conventionally been used in most cases.

For example, a method for detecting an antibody contained in the blood of a cancer patient is described in Patent Literature 1 or 2. This method involves immobilizing an antigen epitope peptide (antigenic peptide composed of several amino acids) onto beads; contacting the beads with the blood components of a subject; and detecting antigen epitope peptide-specific antibody contained in the blood of the subject. The epitope portion to which the antibody binds, however, differs depending on the type of HLA. Use of the method described in Patent Literature 1 or 2 therefore requires clearing various conditions such as the examination of the HLA type of the subject and the identification of an epitope peptide appropriate for the HLA type of the subject.

For preparing a detection reagent for an antibody against a particular antigenic protein, the reagent to be prepared comprises all epitope portions derived from one type of antigenic protein on the surface of one type of bead and performs highly sensitive and stable detection. For this purpose, it is preferred to obtain an antigen having a water-soluble and flexible structure. Nonetheless, most of denatured proteins, poorly soluble proteins (e.g., membrane proteins), or proteins having unstable physical properties tend to aggregate. In this respect, partial peptides capable of exhibiting stable physical properties have conventionally been used in most cases.

Use of such partial peptides requires synthesizing diverse overlapping peptides for covering all epitopes and also requires preparing many types of beads. In addition, it is practically difficult to provide seamless epitope peptides. Even if a full-length antigen having a native structure can be obtained luckily, a general protein, which has a higher-order structure with a hydrophobic moiety buried in the interior, does not always expose its epitope to react with an antibody.

Even in a reagent for antibody detection prepared using solubilized proteins, thiol groups contained in the proteins might form a disulfide bond over time and thereby influence the antibody detection.

For example, Patent Literature 3 describes a method for detecting an anti-HCV antibody contained in the serum of a subject by use of the long-chain polypeptide of human hepatitis C virus (HCV). Patent Literature 3 states that an intraprotein or interprotein disulfide bond generated over time reduces antibody detection sensitivity. The solution to this problem described therein is to dissociate the intraprotein or interprotein disulfide bond using a reducing agent before or during detection, thereby improving the antibody detection sensitivity. Since even the solubilized proteins might precipitate over time, some approach is necessary for solving this problem.

TAPS-sulfonate (trimethylammoniopropyl methanethiosulfonate; hereinafter, referred to as TAPS) is known as a compound that solubilizes proteins. TAPS can bind to thiol groups in a protein to reversibly cationize the protein (see e.g., Non Patent Literatures 1 and 2).

The cationized protein exhibits improved solubility in water. Since the binding of TAPS to the protein is reversible reaction, TAPS is known to dissociate from the protein upon cellular uptake so that the protein can exert its original functions as a result of refolding. Nonetheless, no attempt has been made so far on the process of preparing a reagent for antibody detection by use of solubilization using TAPS. Also, antibodies are generally known to bind to glycosylated proteins. No previous report, however, shows whether an antibody can bind to a protein bound with an artificially synthesized compound such as TAPS.

CITATION LIST

Patent Literature

Patent Literature 1: Japanese Patent No. 3960614 (Immunodia Co., Ltd.)
Patent Literature 2: JP 2005-098877 A (Hitachi Software Engineering Co., Ltd.)
Patent Literature 3: Japanese Patent No. 3225468 (Dainabot Co., Ltd.)

Non Patent Literature

Non Patent Literature 1: M. Seno et al., Growth Factors, 15, 215-229 (1998)
Non Patent Literature 2: M. Inoue et al., Biotechnol. Appl. Biochem., 28, 207-213 (1998)

SUMMARY OF INVENTION

Technical Problem

The present invention has been made in light of the circumstances mentioned above. The present invention provides a method for efficiently producing a reagent for the detection of an antibody present in a liquid sample, the antibody specifically binding to a poorly soluble antigenic protein. The present invention also provides a reagent for antibody detection produced by the production method and use thereof.

Solution to Problem

Specifically, an object of the present invention is to provide the following aspects:

(1) A method for producing a reagent for antibody detection comprising an antigenic protein and a carrier, the method comprising the steps of: solubilizing the antigenic protein by cationization; and allowing the cationized antigenic protein to bind to the carrier.

(2) The method for producing a reagent for antibody detection according to (1), wherein the antigenic protein is a full-length protein.

(3) The method for producing a reagent for antibody detection according to (1) or (2), wherein the antigenic protein is a membrane protein.

(4) The method for producing a reagent for antibody detection according to any one of (1) to (3), wherein the antigenic protein is a cancer antigenic protein.

(5) The method for producing a reagent for antibody detection according to any one of (1) to (4), wherein the cationization is performed by the binding of a cationizing agent to thiol groups of the antigenic protein.

(6) The method for producing a reagent for antibody detection according to (5), wherein the cationizing agent is selected from any one of a thiosulfonate compound, a mixed disulfide compound, a pyridyl sulfide cationizing agent, and an alkyl halide cationizing agent, and mixtures thereof.

(7) The method for producing a reagent for antibody detection according to (6), wherein the thiosulfonate compound is a compound represented by the following formula:

[Formula 1]

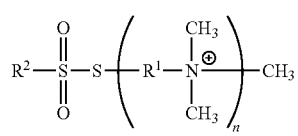

wherein $R^1$ represents a linear alkylene group having 2 to 20 carbon atoms; $R^2$ represents an alkyl group having 1 to 3 carbon atoms; and n represents any integer of 1 to 3.

(8) The method according to (7), wherein the compound is TAPS-sulfonate wherein $R^1$ is —$(CH_2)_3$—; $R^2$ is $CH_3$—; and n is 1.

(9) The method for producing a reagent for antibody detection according to (7), wherein the compound is TAP3S-sulfonate wherein R' is —$(CH_2)_3$—; $R^2$ is $CH_3$—; and n is 3.

(10) The method for producing a reagent for antibody detection according to (6), wherein the alkyl halide cationizing agent is TAP-Br.

(11) The method for producing a reagent for antibody detection according to any one of (1) to (10), wherein the carrier is magnetic beads.

(12) A reagent for antibody detection produced by a method according to any one of (1) to (11).

(13) A method for detecting an antigen-specific antibody contained in a sample, the method comprising the steps of: contacting a reagent for antibody detection according to (12) with the sample; adding thereto an antibody-binding labeled secondary antibody to allow the secondary antibody to bind to the antibody; recovering the reagent for antibody detection; and detecting the reagent for antibody detection bound with the antibody.

(14) The method according to (13), wherein the sample is an isolated body fluid.

The present inventors have completed the present invention by finding that a reagent for antibody detection that is intended to detect an antibody against an antigenic protein can be produced by the configuration as described above.

Advantageous Effects of Invention

A cationizing agent can be used in an antigenic protein solubilization step to thereby efficiently solubilize and recover antigenic proteins. Hence, a reagent for antibody detection comprising a large number of antigenic protein molecules bound with a carrier can be efficiently produced, compared with conventional methods.

Furthermore, this reagent for antibody detection is much more stable than reagents produced by the conventional methods and can thus be stored for a long period.

In one aspect of the present invention, poorly soluble antigenic proteins can be used as antigens for antibody detection. Use of such antigenic proteins permits detection of antibodies even if the antigenic proteins, because of their difference in HLA type, differ in epitope portions which can be recognized by the antibodies. This eliminates the need of producing a plurality of reagents according to the HLA type of a subject and can provide an efficient production method, compared with the methods involving the immobilization of epitope peptides on beads.

In addition, the cationizing agent bound with thiol groups in an antigenic protein can inhibit the time-dependent generation of an intraprotein or interprotein disulfide bond. This can be expected to be effective for preventing reagents for antibody detection from aggregating over time through interprotein disulfide bonds. Thus, the reagents for antibody detection can maintain their functions, compared with the conventional methods, even when poorly soluble antigenic proteins are bound with a carrier or even after long-term storage at room temperature or at 4° C. or −20° C.

On the other hand, such artificially synthesized compounds bound with antigenic proteins might hinder the antigenic proteins from binding to antibodies. However, the present inventors have revealed that antibodies can be detected using antigenic proteins even bound with cationizing agents.

According to these features, a reagent for antibody detection can be efficiently produced by use of the production method of the present invention. The reagent for antibody detection produced by the production method of the present invention can detect an antibody (against an antigenic protein) present in a liquid sample and as such, can detect a cancer antigenic protein-specific antibody from a serum sample, for example, regardless of the HLA type of a cancer patient.

TAPS-sulfonate or TAP-Br, in particular, has a low molecular weight. This compound can therefore minimize steric hindrance that inhibits protein-antibody reaction, while maintaining its high solubilizing ability. This low molecular weight also facilitates the binding of a plurality of its molecules to a protein. As a result, all SH groups contained in the protein can be cationized. This can prevent beads from aggregating during long-term storage. By virtue of these features, the method of the present invention using TAPS-sulfonate or TAP-Br is more effective than the conventional methods.

BRIEF DESCRIPTION OF DRAWINGS

FIG. 9 is a diagram showing results of detecting antibodies against 3 types of cancer antigenic proteins contained in the serum of cancer patients using a reagent for antibody detection produced by the production method of the present invention.

DESCRIPTION OF EMBODIMENTS

Figure 1:
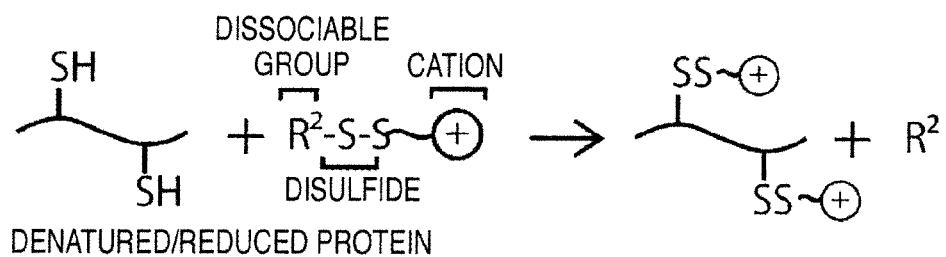
FIG. 1 is a diagram illustrating protein cationization.

Hereinafter, embodiments of the present invention will be described.

First, the method for producing a reagent for antibody detection according to the present invention (hereinafter, also referred to as the production method of the present invention) will be described.

The production method of the present invention is a method for producing a reagent for antibody detection, comprising the steps of: solubilizing the antigenic protein by cationization; and allowing the cationized antigenic protein to bind to the carrier. The antigenic protein may be a poorly soluble protein.

In the present specification, the term "poorly soluble" is provided merely for illustrating a property of the protein and refers to the property of not forming a uniform mixed solution by dissolution in a liquid, particularly, the property of being impossible or difficult to dissolve in water or a physiological solvent. The poorly soluble proteins of types described herein can be defined as poorly soluble proteins when substantially the majorities thereof are recovered into precipitated fractions after centrifugation at 15,100×g for 1 hour of the proteins in water, in water and a salt, or in water and a physiological solvent that does not denature the proteins.

The "protein" described herein includes peptides, polypeptides, and the like. The protein is not limited to naturally occurring proteins that are found in nature and also encompasses recombinant proteins derived from cells transformed by gene transfer or the like, proteins expressed using an in vitro cell-free protein expression system, and synthetic proteins prepared in a synthetic organic chemistry manner. Alternatively, a functional group may be added to a portion or the whole of amino acids constituting the protein in such a way that the amino acid(s) is acetylated, phosphorylated, or methylated, or a portion or the whole of amino acids constituting the protein may be modified with a sugar, a protein, a lipid, or the like.

The "poorly soluble protein" described herein refers to a protein that is impossible or difficult to dissolve even by stirring in water or a physiological solvent at room temperature and may be dissolved by use of, for example, a denaturant but forms precipitates as a result of the replacement of the denaturant with a physiological solvent. Even in the case of a protein that is soluble in nature, the protein of interest is also expressed as a poorly soluble protein when this protein of interest is recovered in the form of an inclusion body by the expression thereof as a recombinant protein using an organism of different species (e.g., by the construction of an expression system in E. coli using a gene recombination technique). Examples of the poorly soluble protein include, but are not limited to, full-length proteins, membrane proteins, and cancer antigenic proteins.

In the present specification, the term "solubilization" refers to the dissolution of a protein in a physiological solvent with its amino acid sequence maintained. The term "solubilization" means that when a solution containing a protein dissolved with a denaturant is centrifuged after replacement with a physiological solvent, the amount of the protein recovered into a supernatant is increased after the centrifugation.

The full-length proteins mean not only natural proteins confirmed to exist in vivo but a protein encoded by the largest open reading frame (ORF) predicted from the genomic sequence. The amino acid sequences of such full-length proteins can be obtained from, but not limited to, database, for example, The ORFeome Collaboration (http://www.orfeomecollaboration.org/) or GeneCards® (http://www.genecards.org/).

The membrane proteins refer to proteins having a transmembrane structure. These proteins are present at the surface of cell membranes, nuclear envelopes, and other intracellular organelles. One protein molecule contains a hydrophilic moiety which is within the cell or is in contact with the outside of the cell, and a hydrophobic moiety which is buried in the cell membrane. For this reason, these membrane proteins, when obtained by expression in E. coli or the like, rarely form a three-dimensional structure in an aqueous solution and tend to form an inclusion body.

The cancer antigenic proteins refer to antigenic proteins that are expressed in tumors and induce immune response or antigenic proteins that can serve as an index for the presence of tumors. Examples of the cancer antigenic proteins include proteins that are expressed at increased levels by the malignant transformation of cells, and proteins having one or some amino acids thereof mutated as a result of the malignant transformation of cells.

A feature of the production method of the present invention is to cationize a protein. More preferably, a feature of the production method of the present invention is to cationize a poorly soluble protein.

The cationization of the protein refers to the addition of excessive positive charges to the protein. The cationized protein exhibits improved solubility in water owing to charge repulsion. Examples of an approach for the protein cationization include the binding of a cationizing agent to a protein.

The "carrier" refers to a material having solid-phase surface to which the antigenic protein is to be bound. Specific examples thereof include, but are not limited to, glass, nylon membranes, semiconductor wafers, and microbeads.

The binding of the antigenic protein to the carrier means that the "antigenic protein" is immobilized directly onto the surface of the carrier using a technique known in the art. Alternatively, the antigenic protein may be immobilized indirectly thereonto via, for example, a biotin-avidin bond or via a linker molecule.

The "sample" refers to a test piece containing the antibody (including subtypes such as IgG, IgA, IgM, IgD, and IgE) and an active fragment thereof (including e.g., Fab and F(ab')$_2$ fragments) to be detected by the reagent for antibody detection according to the present invention.

The "body fluid" refers to a sample in a liquid state that can be collected from an organism. The body fluid corresponds to peripheral blood, bone marrow fluid, cord blood, pleural fluid, ascitic fluid, urine, and the like. The body fluid also corresponds to samples obtained by the treatment of these body fluids according to methods well known to those skilled in the art (e.g., plasma or serum obtained from a supernatant by the centrifugation of peripheral blood).

The "secondary antibody" refers to an antibody and an active fragment thereof that recognizes the antibody (including subtypes such as IgG, IgA, IgM, IgD, and IgE) and an active fragment thereof (including e.g., Fab and F(ab')$_2$ fragments) to be detected by the reagent for antibody detection according to the present invention. The "labeled secondary antibody" refers to a secondary antibody bound with a label such as a radioisotope, a luminescent agent, or a fluorophore. Alternatively, a protein such as an enzyme (such as luciferase or peroxidase), biotin or green fluorescent protein (GFP) may be used as the "label". In the case of such a "label" derived from the protein, the "labeled secondary antibody" may be prepared in a genetic engineering manner as one recombinant protein in the form of a fusion protein.

The cationizing agent that can be used in the production method of the present invention can be any of various compounds that can add positive charges to the protein via disulfide bonds (FIG. 1). For example, a thiosulfonate compound, a mixed disulfide compound, a pyridyl disulfide cationizing agent, or an alkyl halide cationizing agent can be used.

The thiosulfonate compound used in the production method of the present invention is a compound represented by [Formula 2] given below. In this formula, X represents a group having a cation. One group having a cation represented by X may be used, or a linkage of the groups represented by X may be used. In the formula, R$^2$ represents a lower alkyl group having 1 to 3 carbon atoms. Specifically, the thiosulfonate compound used in the production method of the present invention is a thiosulfonate compound having one or more cations derived from X in one molecule. Examples of the group represented by X include quaternary ammonium groups.

[Formula 2]

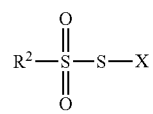

The thiosulfonate compound used in the production method of the present invention is a thiosulfonate compound represented by [Formula 3] given below having one or more quaternary ammonium group-derived cations in one molecule.

[Formula 3]

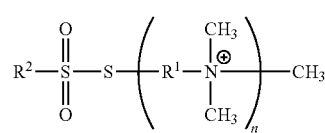

wherein R$^1$ represents a linear or branched alkylene group having 2, 3, 4, 5, 6, 7, 8, 9, 10, 11, 12, 13, 14, 15, 16, 17, 18, 19, or 20 carbon atoms; R$^2$ represents a lower alkyl group having 1, 2, or 3 carbon atoms; and n represents any integer of 1, 2, 3, 4, 5, 6, 7, 8, 9, and 10, more preferably any integer of 1, 2, and 3.

Examples of features of the thiosulfonate compound include an inert dissociable group formed as the dissociable group R$^2$ after protein cationization reaction as illustrated in FIG. 1.

Examples of the compound containing one quaternary ammonium group-derived cation in one molecule include trimethylammoniopropyl methanethiosulfonate (TAPS-sulfonate; hereinafter, referred to as TAPS). Examples of the compound containing three quaternary ammonium group-derived cations in one molecule include TAP3S-sulfonate (hereinafter, referred to as TAP3S).

TAPS refers to a compound represented by [Formula 4] given below. TAPS has a strongly positively charged quaternary amine in the molecule and cationizes a protein through cysteine residue-mediated binding to the protein. The cationized protein exhibits improved solubility and contains stably protected SH groups. TAPS can be synthesized with reference to, for example, Biotechnol. Appl. Biochem. (1998) 28, 207-213 or purchased as a reagent in the form of Br salt (represented by [Formula 5] given below) (molecular weight: 292.26) (from Wako Pure Chemical Industries, Ltd., Katayama Chemical, Ltd., etc.).

[Formula 4]

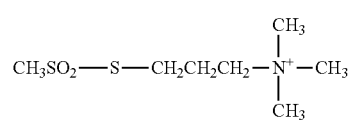

[Formula 5]

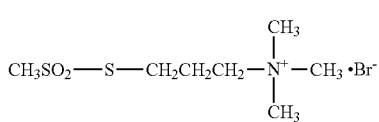

TAP3S refers to a molecular-weight compound represented by [Formula 6] given below. TAP3S has 3 strongly positively charged quaternary amines in the molecule and can more strongly cationize a protein than TAPS. TAP3S can be synthesized with reference to, for example, International Publication No. WO 2011/118731.

[Formula 6]

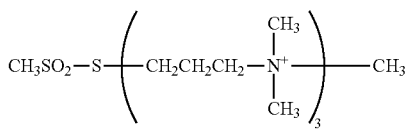

Examples of the mixed disulfide compound used in the production method of the present invention include cystamine as represented by [Formula 7] given below. In the case of cystamine, $NH_3^+$ is the group having a cation.

[Formula 7]

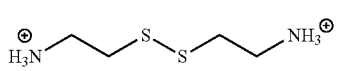

Examples of the pyridyl sulfide cationizing agent used in the production method of the present invention include compounds as represented by [Formula 8] given below. X represents a group having a cation. One group having a cation represented by X may be used, or a linkage of the groups represented by X may be used.

[Formula 8]

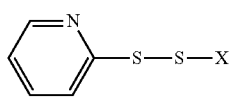

The cationizing agent that can be used in the production method of the present invention may be an alkyl halide cationizing agent that can add positive charges to a protein through S-alkylation. For example, (3-bromopropyl)trimethylammonium (TAP-Br) can be used. TAP-Br irreversibly binds SH groups in a protein and thereby improves its protein-solubilizing ability. TAP-Br (molecular weight: 261.00) can be purchased, for example, as a reagent in the form of Br salt (represented by [Formula 9]) (e.g., from Sigma-Aldrich Corp.).

[Formula 9]

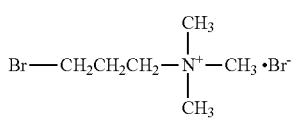

Various cationizing agents can be used in the production method of the present invention. TAPS-sulfonate or TAP-Br, in particular, has a low molecular weight. This compound can therefore minimize steric hindrance that inhibits protein-antibody reaction, while maintaining its high solubilizing ability. This low molecular weight also facilitates the binding of a plurality of its molecules to a protein. As a result, all SH groups contained in the protein can be cationized. This can prevent beads from aggregating during long-term storage.

Hereinafter, the steps of preparing an antigenic protein and preparing a TAPS-bound antigenic protein using TAPS will be described as one example of the obtainment of a cationized antigenic protein.

A gene of the antigenic protein is transferred to *E. coli*, which is then cultured. The cultured *E. coli* is homogenized to recover the antigenic protein. In this recovery, the antigenic protein may be in the form of an inclusion body.

The recovered inclusion body is solubilized with a denaturant. Examples of the denaturant used include, but are not limited to, urea, guanidine hydrochloride, and surfactants.

The antigenic protein thus denatured is treated with a reducing agent to cleave the SS bonds. Examples of the reducing agent include, but are not limited to, dithiothreitol (DTT) and 2-mercaptoethanol (2ME).

TAPS is added to the solution containing the denatured antigenic protein, and the mixture is left standing at room temperature for 30 minutes. The amount of TAPS added is preferably a TAPS molar concentration of 1 to 10 times, more preferably 1.1 to 1.2 times the molar concentration of thiol groups contained in the antigenic protein and the solution.

After 30 minutes, polyethyleneimine having an average molecular weight of 600 is added at a final concentration of 0.2% to the solution containing the TAPS-bound antigenic protein. Then, 10% acetic acid is added thereto in 4 times the amount of the resulting solution. The solution containing the TAPS-bound antigenic protein is centrifuged to recover a supernatant.

Subsequently, the TAPS-bound antigenic protein contained in the supernatant is purified. In the purification, a method such as dialysis or column chromatography can be used. For example, the supernatant is transferred to a dialysis tube and dialyzed against pure water or up to 0.5% acetic acid at 4° C. to remove the denaturant. The dialyzed liquid is centrifuged at 12,000 rpm at 4° C. to room temperature for 15 minutes to recover a supernatant.

The cationized antigenic protein is obtained through these steps.

The cationized antigenic protein exhibits high water solubility, is easily prepared, and exhibits very high stability under weakly acidic conditions (preferably pH 6 or lower, more preferably pH 2 to 5). The cationized antigenic protein therefore can maintain its water solubility in a state where epitopes in its full-length protein are seamlessly exposed. For this reason, all epitopes contained in one antigenic protein can be immobilized on one type of bead so as to facilitate the reaction of the epitopes with antibodies.

Next, the TAPS-bound protein is allowed to bind to a carrier.

In one aspect, magnetic beads, non-magnetic beads, a microplate, or the like can be used as the carrier. Magnetic beads are preferably used in terms of convenient analysis operation. Hereinafter, a case using the beads as the carrier will be described.

The beads are suspended in a solution for binding. In the case where the beads have already been modified to help the beads bind to the protein, the beads are bound directly to the TAPS-bound protein. In the absence of such modification to help the beads bind to the protein, the beads are modified with a material, such as skimmed milk, which does not inhibit the reaction of the TAPS-bound protein with an antibody during antibody detection.

The solution of the TAPS-bound protein is mixed with the suspension of the beads. For example, 2 to 16 hours are preferred as the mixing time of beads activated into a state reactive with amino groups.

The beads are recovered, then suspended in a solution for washing, and washed by centrifugation. Examples of the solution for washing include phosphate buffer solutions. For storing the beads thus washed, the beads are suspended in a buffer for storage and stored. Examples of the buffer for storage include a storage buffer available from Bio-Rad Laboratories, Inc. A weakly acidic (preferably pH 6 or lower, more preferably pH 2 to 5) buffer for storage more stably maintains the solubility of the TAPS-bound protein.

The reagent for antibody detection can be produced through these steps.

Next, an antibody detection method will be described in detail as one aspect using the reagent for antibody detection produced by the production method of the present invention (hereinafter, referred to as the reagent of the present invention).

The reagent of the present invention may be a reagent for antibody detection comprising a cationized poorly soluble antigenic protein and beads.

A sample presumed to contain an antibody is obtained from a subject. A body fluid can be used as the sample. Peripheral blood, bone marrow fluid, cord blood, pleural fluid, ascitic fluid, urine, or the like can be used as the body fluid. Peripheral blood is preferably used in consideration of easy collection and a small burden on the subject. The amount of the sample collected is preferably an amount that puts no heavy burden on the subject. The peripheral blood can be collected by use of a whole blood collection method using a vacuum blood collection tube, a blood collection bag, or the like. For blood collection, heparin or the like may be added in order to prevent the coagulation of blood.

Plasma is collected from the collected blood by centrifugation. Alternatively, the plasma may be obtained during the partial collection of blood by use of an apheresis apparatus.

Also, peripheral blood may be collected, and serum can be obtained by the removal of blood cell components and blood-clotting components and also used as the sample.

For antibody detection, the plasma or the serum is diluted, if necessary.

The reagent of the present invention is mixed with the plasma. The mixing time is preferably approximately 2 hours, for example, for reaction at room temperature or overnight reaction at 4° C. The reagent of the present invention is recovered using a centrifugation method or a magnetic apparatus and washed.

There may be apprehension that the cationization influences antigen-antibody reaction. In such a case, the influence can be easily tested, because the cationization can be canceled by treatment with a reducing agent such as dithiothreitol.

For antibody detection, a secondary antibody is allowed to bind to the antibody. In the case of, for example, a human subject, the antibody bound with the reagent of the present invention is a human antibody. Thus, a labeled anti-human antibody is used as the secondary antibody for labeling. Examples thereof include biotinylated anti-human IgG mouse monoclonal antibodies.

The beads bound with the secondary antibody detected using a flow cytometer. Bio-Flex (Bio-Rad Laboratories, Inc.), in which beads themselves are stained, may be used in the detection. In such a case, plural types of beads can be applied simultaneously to an apparatus. Thus, plural types of antibodies can be analyzed by one operation. This can shorten the analysis time.

An antibody can also be detected from other liquid samples using the reagent of the present invention in the same way as described in the above paragraphs except that the plasma is changed to the liquid samples such as serum.

The analysis of an antibody contained in the blood of a subject according to these embodiments presumably achieves the following situations:

The allergenic reactivity of the subject is determined by the analysis of in vivo antibodies in the subject.

An antibody that correlates with therapeutic effects or a progress after treatment is found by antibody analysis conducted before and after the treatment. The antibody thus found is used as an index to decide a therapeutic strategy or to predict or determine prognosis.

For immune cell therapy, an antigen whose specific antibody has been detected in the serum of a patient is used in the treatment to thereby improve therapeutic effects.

Before and after radiotherapy, antibodies are analyzed to thereby predict therapeutic effects reportedly involving immune functions, such as abscopal effects.

Although the effects mentioned above may be attained by a reagent for antibody detection using an epitope peptide, the reagent of the present invention is superior in that proteins can be used. This is because use of the proteins allows antibodies to be detected without being limited by the HLA type of a subject. As a result, even an HLA type that is generally regarded as being minor and thus less understood in epitope peptide analysis can be analyzed.

Example 1

Hereinafter, the present invention will be described in detail with reference to Examples. However, the present invention is not intended to be limited by these Examples by any means, as a matter of course.

<Study on Large-Scale Culture and Preparation Methods for MAGE-A4 and WT-1>

First, each antigenic protein for use in antibody detection was prepared.

*E. coli* T7 Express was transformed with each of 2 types of plasmid DNAs of His-tag-fused MAGE-A4 (SEQ ID NOs: 16 and 17, antigenic protein sequence: SEQ ID NOs: 3 and 4) and His-tag-fused WT-1 (SEQ ID NOs: 14 and 15, antigenic protein sequence: SEQ ID NOs: 1 and 2) cloned into pET28b vectors. Several colonies formed on a plate were picked up, then added to 10 mL of an LB/Kan25 medium, and shake-cultured for 2 hours.

Next, a small amount of the cultures was added to 400 mL of a TB medium and further cultured at 37° C. When the bacterial cell concentration reached OD600=0.7 to 0.8, IPTG was added thereto at a final concentration of 0.5 mM. The cells were further cultured at 37° C. for 3 hours.

The bacterial cells were dispersed using a sonicator in 40 mL of a lysis buffer (20 mM Tris-HCl (pH 8.0), 50 mM NaCl, 5 mM $MgSO_4$, and 0.2% Tween 20) and further homogenized by 1 minute×3 sets.

To the solution containing the bacterial cell homogenates, 1 μL of a strong nuclease Benzonase (HC) was added, and the mixture was left standing at room temperature for approximately 15 minutes.

For WT-1, precipitates (inclusion body) were recovered by centrifugation (8 krpm, 10 to 15 min, room temperature), while the supernatant was removed. To the recovered precipitates, 50 to 100 mL of RO water was added, and the precipitates were resuspended using a sonicator and recovered by centrifugation (8 krpm, 10 to 15 min, room temperature).

For MAGE-A4, a supernatant was recovered by centrifugation (8 krpm, 10 to 15 min, room temperature).

<Solubilization of WT-1 by Reversible Cationization Method of Denatured Precipitated Fraction>

The precipitates were dissolved in 5 to 10 mL of 6 M guanidine and 0.1 M Tris-HCl (pH 8)+1 mM EDTA. After deaeration and nitrogen substitution, 30 mM DTT (solid) was added thereto, followed by treatment at 37° C. for approximately 1 hour.

To the solution containing WT-1, 70 mM TAPS-sulfonate was added, followed by treatment at 37° C. for approximately 30 minutes.

Figure 2:
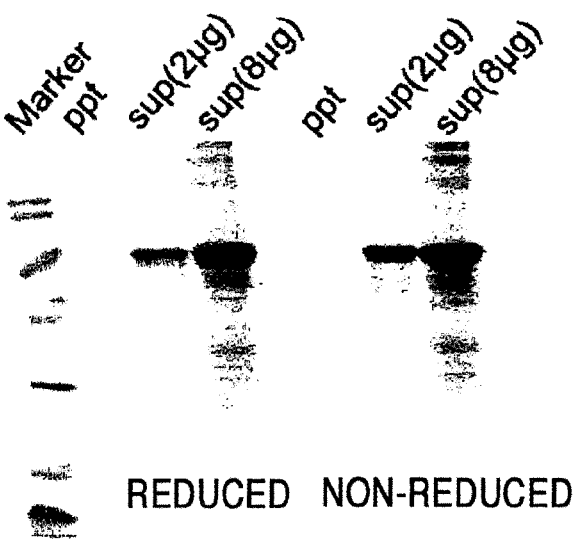
FIG. 2 is a diagram showing results of SDS-PAGE analysis after cationization of WT-1 with TAPS.

To the solution containing WT-1 and TAPS-sulfonate, acetic acid in an amount of 1/10 thereof and 0.1% PEI600 were added, and the mixture was then well dialyzed against Milli-Q water at 4° C. After the dialysis, SDS-PAGE was performed. The results are shown in FIG. 2. The lane indicated by sup depicts the migration of the solution thus dialyzed. The lane indicated by ppt depicts the migration of a sample obtained as an insoluble fraction after the dialysis. The lane indicated by "Reduced" depicts the migration of the protein separated from TAPS by the addition of a reducing agent to the sample. The lane indicated by "Non-reduced" depicts the migration of the TAPS-bound protein without the addition of a reducing agent to the sample. The SDS-PAGE analysis results shown in FIG. 2 demonstrated that WT-1 was successfully TAPS-bound and solubilized.

<His-Tag Purification of MAGE-A4 Using $Co^{2+}$ Column>

A $Co^{2+}$ column was equilibrated with solution A (20 mM Tris-HCl (pH 8.0), 50 mM NaCl, and 0.2% Tween 20). Then, the supernatant of MAGE-A4 was adsorbed onto the resin. Then, the resin was thoroughly washed with solution A. Next, 30 mL of solution A+5 mM imidazole was injected thereto. After addition of 4 mL of solution A+200 mM imidazole, the column was left standing for 5 minutes, followed by protein elution. This operation was repeated five times to recover purified MAGE-A4.

<Binding of TAPS to MAGE-A4>

MAGE-A4 thus affinity-purified was added to an eggplant-shaped flask, then dehydrated using a freeze dryer, and dissolved in 3 mL of 6 M guanidine and 0.1 M Tris-HCl (pH 8). After deaeration and nitrogen substitution, 30 mM DTT (solid) was added thereto, followed by treatment at 37° C. for approximately 1 hour. To the solution containing MAGE-A4, 70 mM TAPS-sulfonate was added, followed by treatment at 37° C. for approximately 30 minutes.

Figure 3:
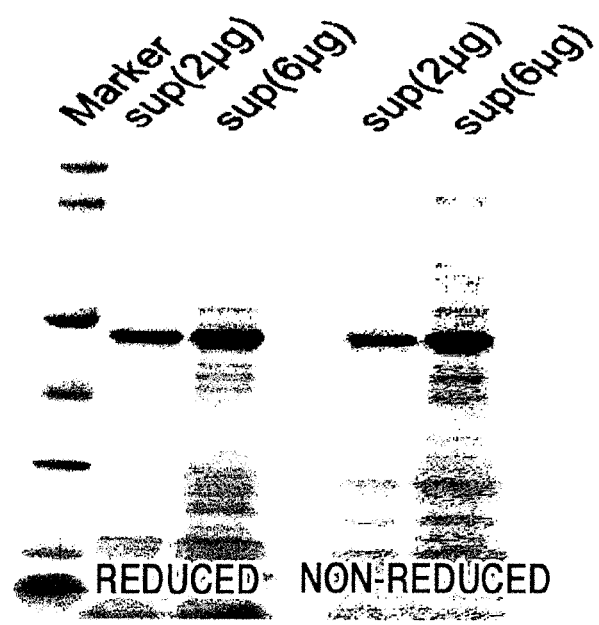
FIG. 3 is a diagram showing results of SDS-PAGE analysis after cationization of MAGE-A4 with TAPS.

To the solution containing MAGE-A4 and TAPS-sulfonate, acetic acid in an amount of 1/10 thereof and 0.1% PEI600 were added, and the mixture was then well dialyzed against Milli-Q water at 4° C. After the dialysis, SDS-PAGE was performed. The results are shown in FIG. 3.

<HPLC Purification>

Figure 4:
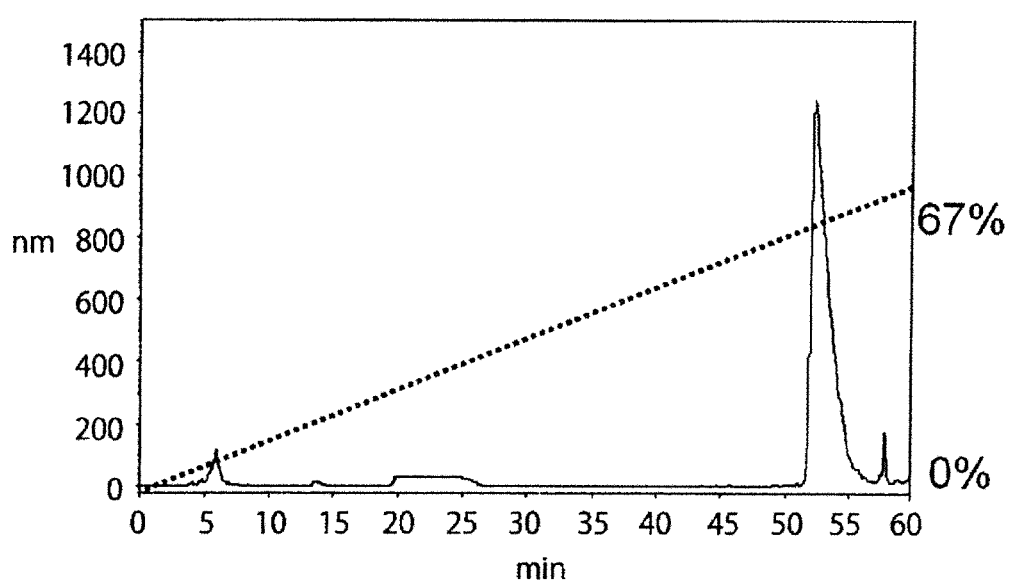
FIG. 4 is a diagram showing results of HPLC purification of TAPS-bound WT-1.
Figure 5:
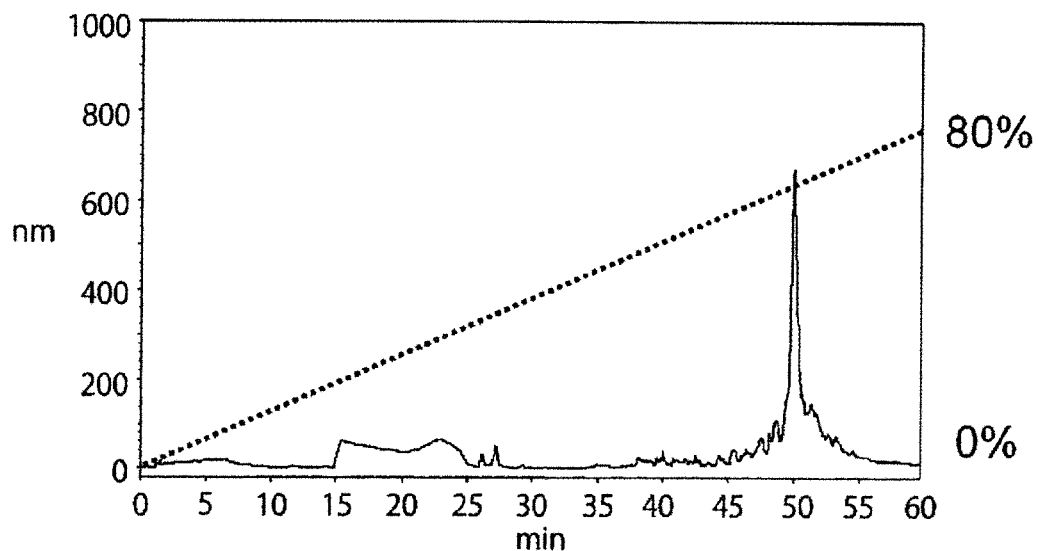
FIG. 5 is a diagram showing results of HPLC purification of TAPS-bound MAGE-A4.

TAPS-bound MAGE-A4 and WT-1 were purified using reverse-phase HPLC. The chromatograms are shown in FIGS. 4 and 5.

Figure 6:
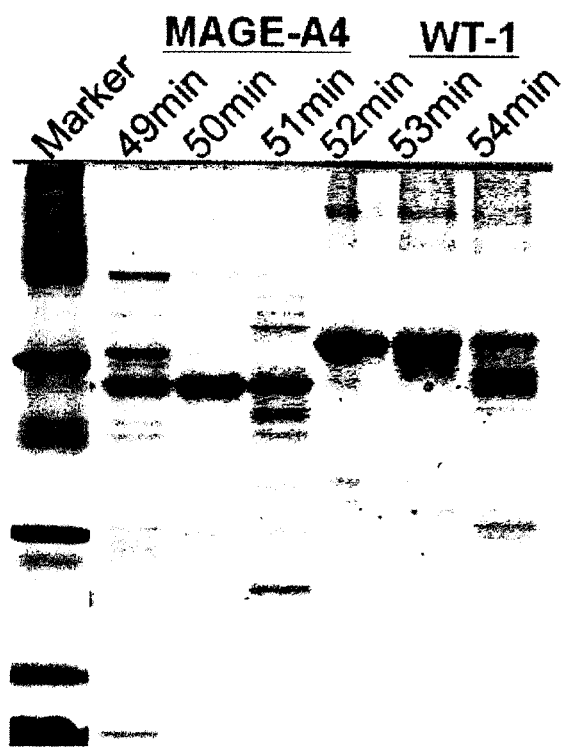
FIG. 6 is a diagram showing results of SDS-PAGE analysis after HPLC purification of TAPS-bound WT-1 and MAGE-A4. Min represents an elution time in the HPLC purification (FIG. 4 or 5). For example, the lane indicated by "49 min" depicts the migration of fractions collected for 1 minute from the elution time of 49 minutes.

After HPLC, TAPS-bound MAGE-A4 and WT-1 were analyzed by SDS-PAGE. The results are shown in FIG. 6. The analysis results demonstrated that a highly pure antigenic protein can be prepared by the reverse-phase HPLC purification of the TAPS-bound protein. Fractions were recovered as MAGE-A4 at elution times of 50 minutes to 51 minutes (lane "50 min" in FIG. 6), while fractions were recovered as WT-1 at elution times of 52 minutes to 53 minutes (lane "52 min" in FIG. 6). These fractions were used in the subsequent steps.

Figure 7:
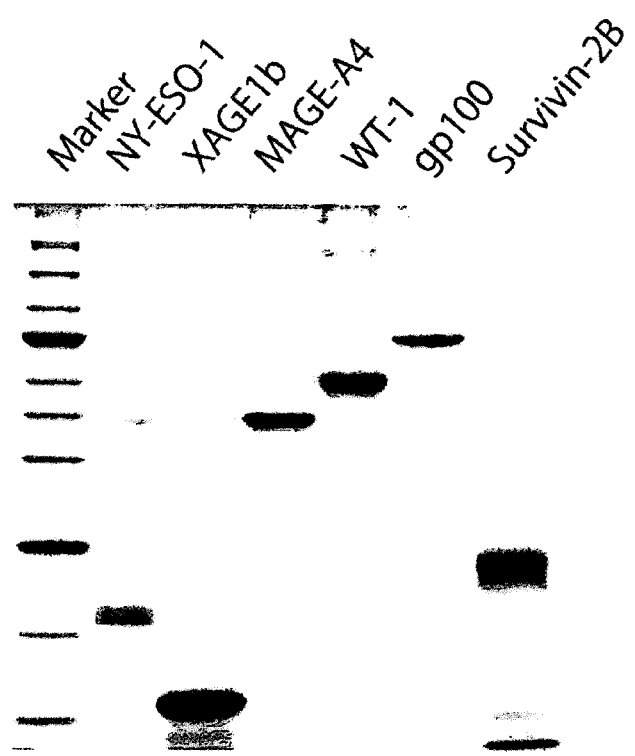
FIG. 7 is a diagram showing results of SDS-PAGE analysis of prepared antigenic proteins. Each lane was charged with 2 μg of each antigenic protein.

His-tag-fused NY-ESO-1 (SEQ ID NOs: 18 and 19, antigenic protein sequence: SEQ ID NOs: 5 and 6), XAGE1b (SEQ ID NOs: 20 and 21, antigenic protein sequence: SEQ ID NOs: 7 and 8), gp100 (SEQ ID NOs: 22 and 23, antigenic protein sequence: SEQ ID NOs: 9 and 10), Survivin-2B (SEQ ID NOs: 24 and 25, antigenic protein sequence: SEQ ID NOs: 11 and 12) were prepared by the same method as that for WT-1. The prepared proteins were analyzed by SDS-PAGE. The results are shown in FIG. 7.

<Binding to Bio-Plex COOH Beads (Manufactured by Bio-Rad Laboratories, Inc.)>

The antigens were immobilized onto 6 types of Bio-Plex COOH beads (amount of 1/10 ($1.25 \times 10^6$ beads)) using Bio-Plex amine coupling kit (manufactured by Bio-Rad Laboratories, Inc.). All of the antigens used were antigens in a denatured state solubilized by TAPS binding (11 μg each).

Each solubilized protein was dissolved in a buffer and left standing on ice.

The container of the COOH beads was shaken for 30 seconds with a vortex mixer, and the beads were suspended by sonication for 30 seconds.

The COOH bead suspension was centrifuged at 14,000×g for 4 minutes to remove a supernatant.

To the recovered precipitates, 100 μL of a bead wash buffer was added. The mixture was shaken for 10 seconds with a vortex mixer, and the beads were suspended by sonication for 10 seconds. The COOH bead suspension was centrifuged at 14,000×g for 4 minutes to remove a supernatant.

To the recovered precipitates, 80 μL of a bead activation buffer was added. The mixture was well shaken for 30 seconds with a vortex mixer, and the beads were suspended by sonication for 30 seconds.

To the COOH bead suspension, 10% of 50 mg/mL EDAC was added, and then, 10 μL of 50 mg/mL S—NHS (N-hydroxysulfosuccinimide) was added. The COOH bead suspension was shaken for 30 seconds with a vortex mixer.

While the beads were shielded from light, the COOH bead suspension was shaken for 20 minutes in a rotary incubator.

To the COOH bead suspension, 150 μL of PBS was added, and the mixture was shaken for 10 seconds with a vortex mixer. The COOH bead suspension was centrifuged at 14,000×g for 4 minutes to remove a supernatant. This operation was repeated again.

To the recovered precipitates, 100 μL of PBS was added. The mixture was shaken for 30 seconds with a vortex mixer, and the beads were suspended by sonication for 15 seconds.

The COOH bead suspension was mixed with the TAPS-bound protein suspension. The total amount of the mixture was adjusted to 500 μL by the addition of PBS.

While the beads were shielded from light, the COOH bead suspension was shaken at room temperature for 2 hours in a rotary incubator.

The suspension containing the COOH beads and the TAPS-bound protein was centrifuged at 14,000×g for 4 minutes to remove a supernatant.

The COOH beads (on which the TAPS-bound protein was immobilized) recovered as precipitates were washed by the addition of 500 μL of PBS. The COOH bead suspension was centrifuged at 14,000×g for 4 minutes to remove a supernatant.

The COOH beads recovered as precipitates were resuspended by the addition of 250 μL of a blocking buffer. The COOH bead suspension was shaken for 15 seconds with a vortex mixer.

While the COOH beads were shielded from light using an aluminum foil, the COOH bead suspension was shaken at room temperature for 30 minutes in a rotary incubator.

The COOH bead suspension was centrifuged at 14,000×g for 4 minutes to remove a supernatant.

The COOH beads recovered as precipitates were resuspended by the addition of 500 μL of a buffer for storage. The COOH bead suspension was centrifuged at 16,000×g for 6 minutes to remove a supernatant.

The TAPS-bound protein-immobilized beads thus obtained were suspended in 150 μL of a storage buffer and stored therein. Table 1 shows the concentration of each type of bead.

TABLE 1

| Cancer antigenic protein | Bead No | Bead concentration (the number of beads/mL) |
|---|---|---|
| NY-ESO-1 | 26 | $4.33 \times 10^6$ |
| XAGE1b | 28 | $5.59 \times 10^6$ |
| MAGE-A4 | 43 | $3.68 \times 10^6$ |
| WT-1 | 45 | $1.95 \times 10^6$ |
| gp100 | 62 | $6.09 \times 10^6$ |
| Survivin-2B | 64 | $1.61 \times 10^6$ |

Example 2

Analysis of Antibody Contained in Serum of Cancer Patient—1

Blood was collected from two cancer patients (Donor 1 and Donor 2), and serum was obtained therefrom.

Six types of magnetic beads on which the antigenic proteins (NY-ESO-1, WT-1, MAGE-A4, XAGE1b, gp100, and Survivin-2B) were respectively immobilized were mixed at the same concentrations and dispensed to the wells of a 96-well plate (Bio-Rad Laboratories, Inc., #171-025001). The serum of each patient was added to each well. While shielded from light using an aluminum foil, the plate was shaken at room temperature for 1 hour for reaction. The beads were washed with Wash Station (Bio-Rad Laboratories, Inc.). For antibody detection, biotinylated anti-human IgG (H+L) (manufactured by Vector Laboratories, Inc., BA-3000) was added as a secondary antibody to each well. While shielded from light using an aluminum foil, the plate was shaken at room temperature for 30 minutes for reaction. The beads were washed with Wash Station (Bio-Rad Laboratories, Inc.). (R-)Phycoerythrin (PE)-labeled streptavidin (Vector Laboratories, Inc.) was added to each well. While shielded from light using an aluminum foil, the plate was shaken at room temperature for 10 minutes for reaction. The beads were washed with Wash Station (Bio-Rad Laboratories, Inc.) and analyzed using Bio-Plex (Bio-Rad Laboratories, Inc.). The serum of each patient used was diluted 400-fold, 1600-fold, and 6400-fold.

Figure 8:
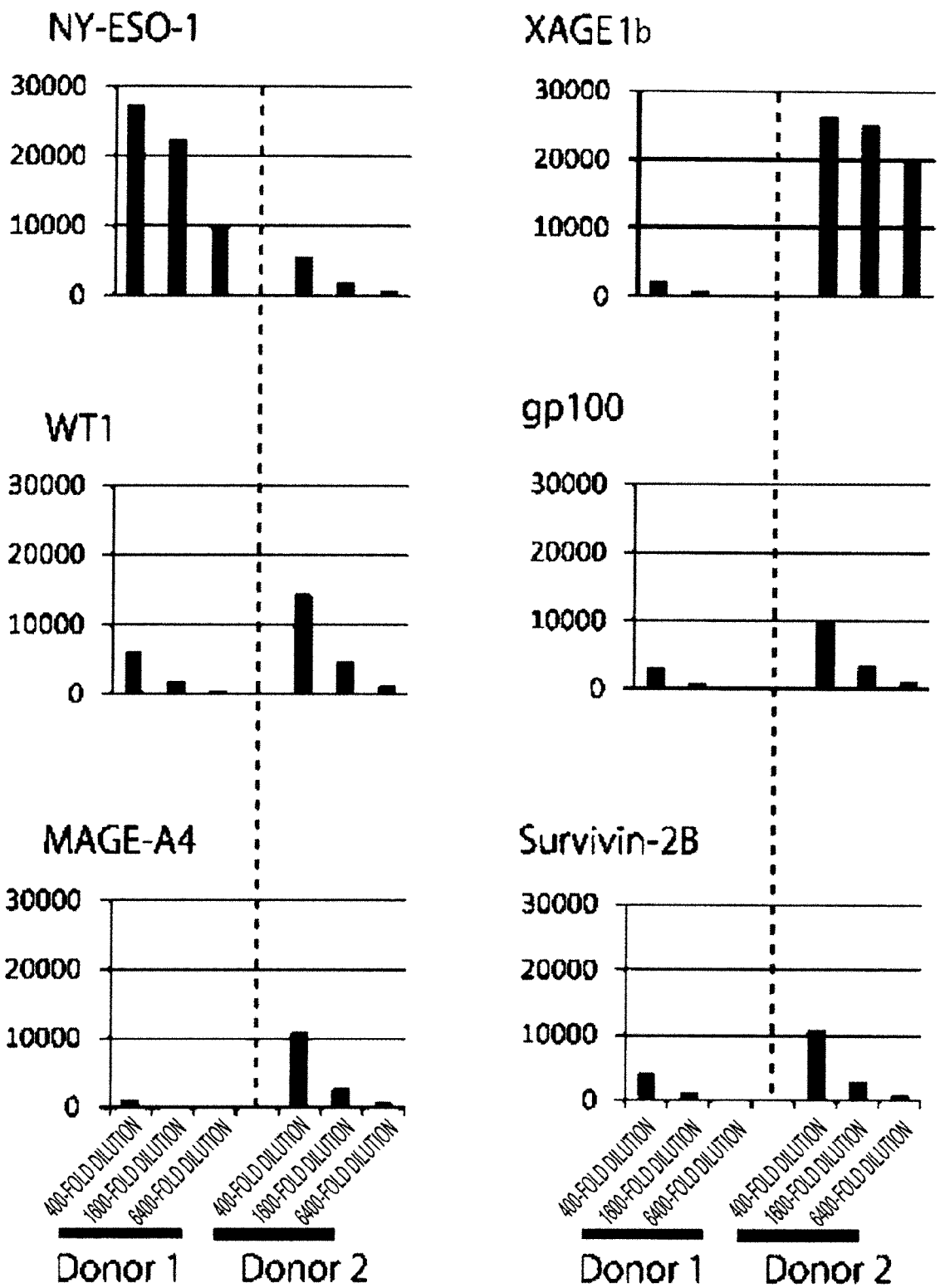
FIG. 8 is a diagram showing results of detecting antibodies against 6 types of cancer antigenic proteins contained in the serum of cancer patients using a reagent for antibody detection produced by the production method of the present invention.

As shown in FIG. 8, the sample derived from Donor 1 was confirmed to respond to NY-ESO-1.

This result suggested that: the blood of Donor 1 contained an antibody recognizing NY-ESO-1; cancer in Donor 1 expressed NY-ESO-I; and peptide vaccine or DC vaccine therapy using NY-ESO-1 was possibly effective for Donor 1.

As a result of this test, the sample derived from Donor 2 was confirmed to respond to XAGE1b.

This result suggested that: the blood of Donor 2 contained an antibody recognizing XAGE1b; cancer in Donor 2 expressed XAGE1b; and peptide vaccine or DC vaccine therapy using XAGE1b was possibly effective for Donor 2.

Example 3

Analysis of Antibody Contained in Serum of Cancer Patient—2

Serum was obtained from 8 renal cell cancer patients (Donor 2 to Donor 9) before and after EP-DC therapy.

The EP-DC therapy refers to a treatment method which involves: preparing lysates by the freeze-thaw method or the like from tumor tissues removed by surgery from a cancer patient; electroloading the lysates into dendritic cells; and administering the dendritic cell vaccine thus prepared to the patient.

Six types of magnetic beads on which the antigenic proteins were respectively immobilized were mixed at the same concentrations and dispensed to the wells of a 96-well plate (Bio-Rad Laboratories, Inc., #171-025001). The serum of each patient was added to each well. While shielded from light using an aluminum foil, the plate was shaken at room temperature for 1 hour for reaction. The beads were washed with Wash Station (Bio-Rad Laboratories, Inc.). For antibody detection, biotinylated anti-human IgG (H+L) (manufactured by Vector Laboratories, Inc., BA-3000) was added as a secondary antibody to each well. While shielded from light using an aluminum foil, the plate was shaken at room temperature for 30 minutes for reaction. The beads were washed with Wash Station (Bio-Rad Laboratories, Inc.). PE-labeled streptavidin (Vector Laboratories, Inc.) was added to each well. While shielded from light using an aluminum foil, the plate was shaken at room temperature for 10 minutes for reaction. The beads were washed with Wash Station (Bio-Rad Laboratories, Inc.) and analyzed using an assay apparatus of Bio-Plex (Bio-Rad Laboratories, Inc.). The serum of each patient used was diluted 400-fold, 1600-fold, and 6400-fold.

As shown in FIG. 9, the serum of Donor 6 and Donor 8 was confirmed to respond to MAGE-A4. Accordingly, the blood of Donor 6 and Donor 8 contained an antibody recognizing MAGE-A4, suggesting that the in vivo tumor tissues of the patients Donor 6 and Donor 8 possibly expressed MAGE-A4. In this case, peptide vaccine or DC vaccine therapy using MAGE-A4 was presumably appropriate for these patients.

Figure 10:
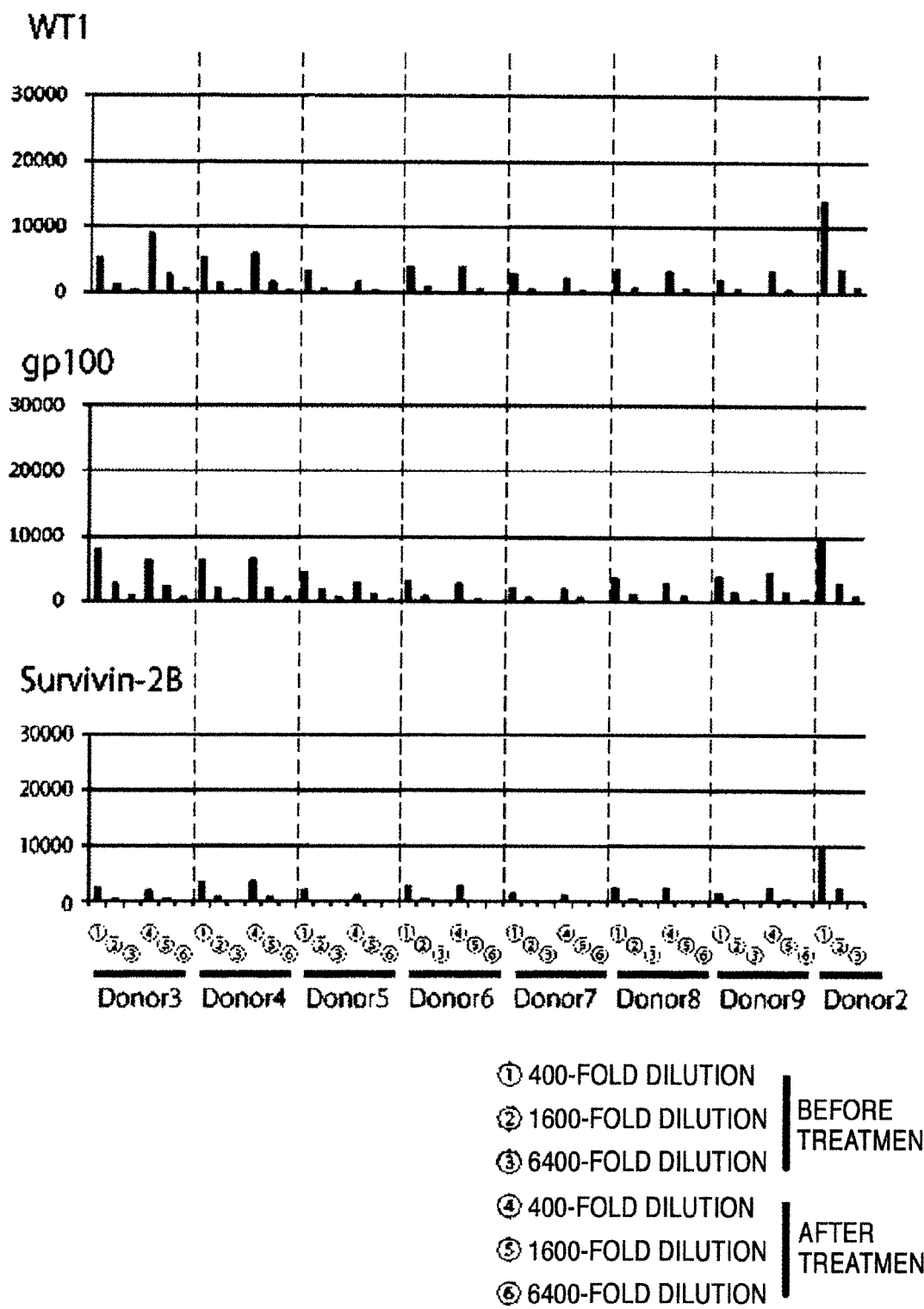
FIG. 10 is a diagram showing results of detecting antibodies against 3 types of cancer antigenic proteins contained in the serum of cancer patients using a reagent for antibody detection produced by the production method of the present invention.

As shown in FIG. 10, the serum of Donor 3 was confirmed to respond more highly to WT-1 after DC vaccine therapy compared with before the therapy. Accordingly, the blood of Donor 3 contained an antibody recognizing WT-1, suggesting that the tumor tissues of Donor 3 possibly expressed WT-1. In this case, peptide vaccine or DC vaccine therapy using WT-1 was presumably appropriate for this patient.

Example 4

Evaluation of Cationizing Reagent for its Ability to Protect SH Group

Chicken egg white lysozyme (SEQ ID NO: 13; hereinafter, also simply referred to as lysozyme; manufactured by Kewpie Corp.) was used as a sample to evaluate the ability of a cationizing reagent to protect SH groups.

15 mg of the lysozyme was weighed into a 100-mL pear-shaped flask and dissolved in 2 mL of 6 M guanidine hydrochloride, 0.1 M Tris-HCl (pH 8.5), and 2 mM EDTA. After deaeration and nitrogen substitution of the obtained solution, dithiothreitol (DTT) was added thereto at a final concentration of 30 mM, and the mixture was reacted for 2 hours in a thermostat bath of 37° C. To the obtained reduced lysozyme, each cationizing reagent (TAPS-sulfonate (manufactured by Katayama Chemical, Ltd.) or TAP3S-sulfonate) was added at a final concentration of 70 mM, and the mixture was further reacted at room temperature for 2 hours. The reaction was stopped by the addition of acetic acid in 1/10 of the amount of the obtained solution. Then, the solution was dialyzed against Milli-Q water at 4° C. for 1 day to obtain TAPS-bound lysozyme and TAP3S-bound lysozyme. The TAP3S-sulfonate used was synthesized according to the approach described in Japanese Patent Application No. 2010-070804.

TAPS-bound, TAP3S-bound, native, and reduced lysozymes were subjected to reverse-phase HPLC (high-performance liquid chromatography). The native lysozyme contains four SS bonds in one molecule, and has hydrophilicity to some extent because its hydrophobic groups are not exposed. The reduced lysozyme is a denatured protein with its SS bonds reduced and has the highest hydrophobicity (lowest solubility in water). The column used was COSMO-SIL Protein-R (manufactured by Nacalai Tesque, Inc.). The solvent used was acetonitrile diluted with 0.1% hydrochloric acid, and the acetonitrile concentration was set to 1% to 50%.

Figure 11:
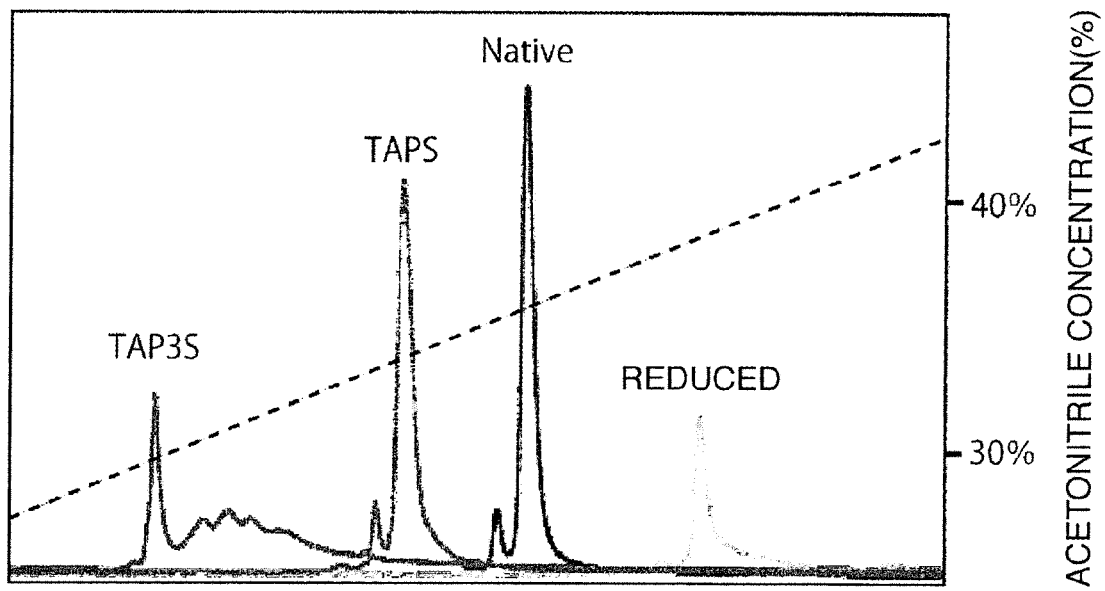
FIG. 11 is a diagram showing results of reverse-phase HPLC (high-performance liquid chromatography) performed on TAPS-bound, TAP3S-bound, native, and reduced lysozymes.

The results summarizing reverse-phase HPLC charts are shown in FIG. 11. The straight line represents the concentrations of acetonitrile. Peaks positioned closer to the left side mean lower hydrophobicity (higher solubility in water) of samples. The TAP3 S-bound lysozyme was more hydrophilic than the native and reduced lysozymes and was eluted with a low-concentration acetonitrile solvent. TAP3S, however, has the difficulty in protecting and cationizing all of the 8 SH groups in the lysozyme and showed peak dispersion due to contamination by imperfect products in which a portion of SH groups was unprotected. By contrast, in the TAPS-bound lysozyme, all of the 8 SH groups were protected and cationized, demonstrating high homogeneity. Such a difference in the ability to protect SH groups between TAPS and TAP3S is attributed to the sizes of their molecules. This is presumably because, in the case of protecting somewhat dense SH groups on a protein molecule, the large TAP3S molecule causes steric hindrance on the protein molecule to be cationized, resulting in a trace amount of residual SH groups incapable of binding to TAP3S; thus, the subsequent SH/SS exchange reaction proceeds slowly.

Example 5

Evaluation of Storage Stability of Beads

When a reagent for antibody detection is prepared and stored in a state where the SH groups of the protein are incompletely protected, it is possible that unprotected residual SH groups form SS bonds to cause the aggregation of proteins or the aggregation of reagents for antibody detection. Thus, the storage stability of the reagent for antibody detection was confirmed by the following procedures.

According to the procedures described in Example 1, TAPS-bound, TAP3S-bound, or native MAGE-A4 was prepared, and beads on which each protein was immobilized were prepared.

The prepared beads were suspended in a buffer for storage and stored under conditions of 4° C. or 37° C. After a lapse of given time, the abundance of bead aggregates among the beads in the suspension was measured using a hemocytometer. The percentage of bead aggregates shown in the results was calculated according to the number of aggregates each involving 3 or more beads/the total number of beads×100.

Figure 12:
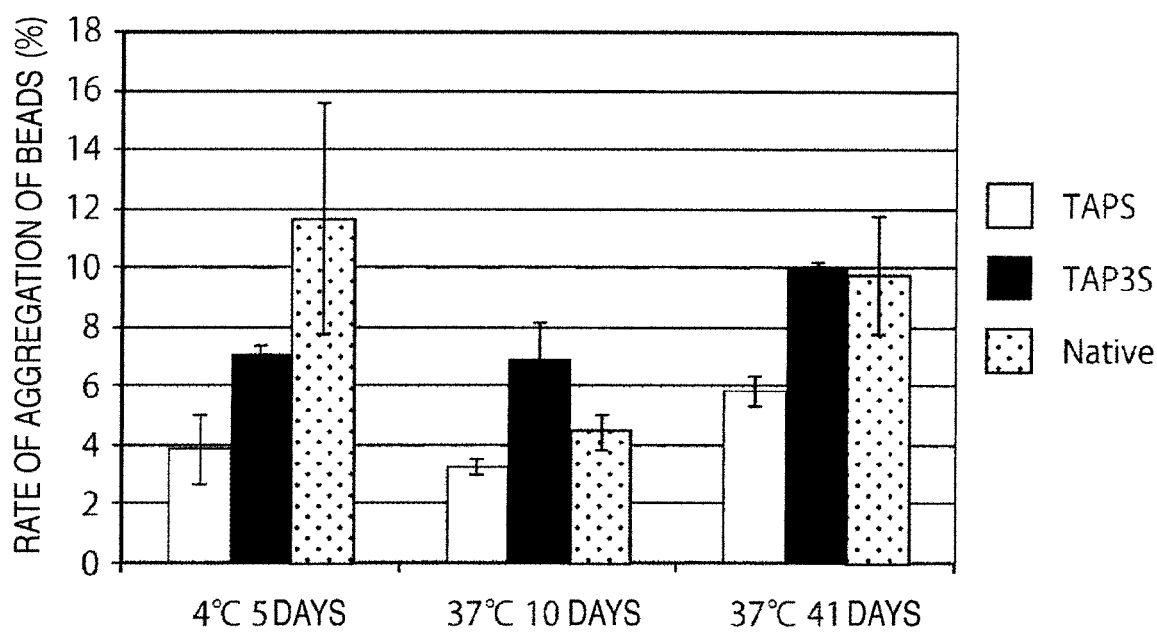
FIG. 12 is a diagram showing the percentages of bead aggregates contained in suspensions of TAPS-bound, TAP3S-bound, native, and reduced MAGE-A4-immobilized beads stored at 4° C. for 5 days or at 37° C. for 10 days or 41 days.

FIG. 12 shows the percentage of bead aggregates contained in each suspension stored at 4° C. for 5 days or at 37° C. for 10 days or 41 days. In the case of storage at 4° C., the percentage of bead aggregates was decreased in the stored TAPS-bound or TAP3 S-bound MAGE-A4-immobilized beads compared with the stored native MAGE-A4-immobilized beads. In the case of storage at 37° C., the percentage of bead aggregates was decreased in the stored TAPS-bound MAGE-A4-immobilized beads compared with the stored native MAGE-A4-immobilized beads.

Next, the bead storage solution was subjected to SDS-PAGE in order to confirm that this decrease in the percentage of bead aggregates was not attributed to the liberation of the immobilized antigenic protein from the beads.

MAGE-A4 immobilized on the beads was N-terminally His-tagged. Thus, liberated MAGE-A4 proteins in the storage solution of the MAGE-A4-immobilized beads were detected by Western blotting using an anti-His-tag antibody (OGHis, manufactured by Medical & Biological Laboratories Co., Ltd. (MBL)).

Figure 13:
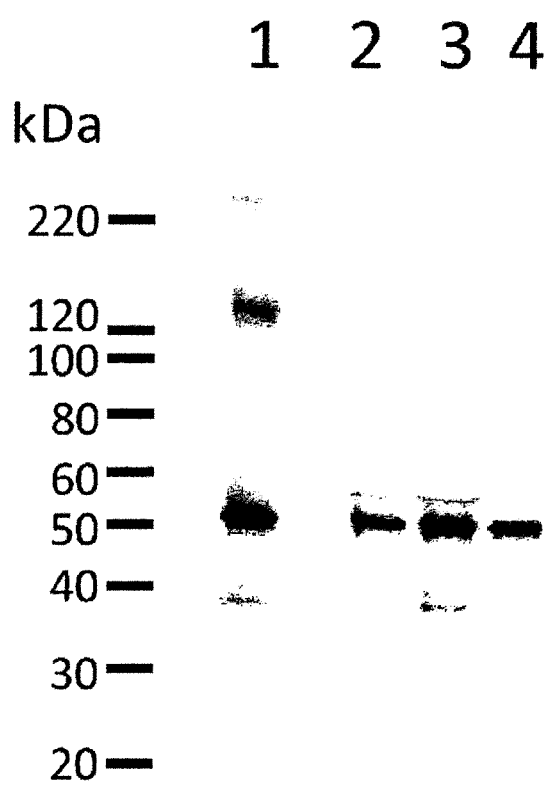
FIG. 13 is a diagram showing results of Western blotting performed on storage solutions of TAPS-bound MAGE-A4-immobilized beads (lane 2), TAP3 S-bound MAGE-A4-immobilized beads (lane 3), and native MAGE-A4-immobilized beads (lane 4) stored for 104 days. Lane 1 depicts the migration of 100 ng of the MAGE-A4 protein as a control.

The results are shown in FIG. 13. The storage solutions of the TAPS-bound MAGE-A4-immobilized beads, the TAP3S-bound MAGE-A4-immobilized beads, and the native MAGE-A4-immobilized beads stored for 104 days were used as the samples migrated in lanes 2, 3, and 4, respectively. Free proteins were detected at the same levels among all of these samples, demonstrating the absence of the phenomenon in which cationization facilitates the liberation of antigenic proteins from beads.

In addition, bound proteins were detected as to Bio-Plex COOH beads, the TAPS-bound MAGE-A4-immobilized beads stored for 104 days, the TAP3S-bound MAGE-A4-immobilized beads stored for 104 days, and the native MAGE-A4-immobilized beads stored for 104 days.

Figure 14:
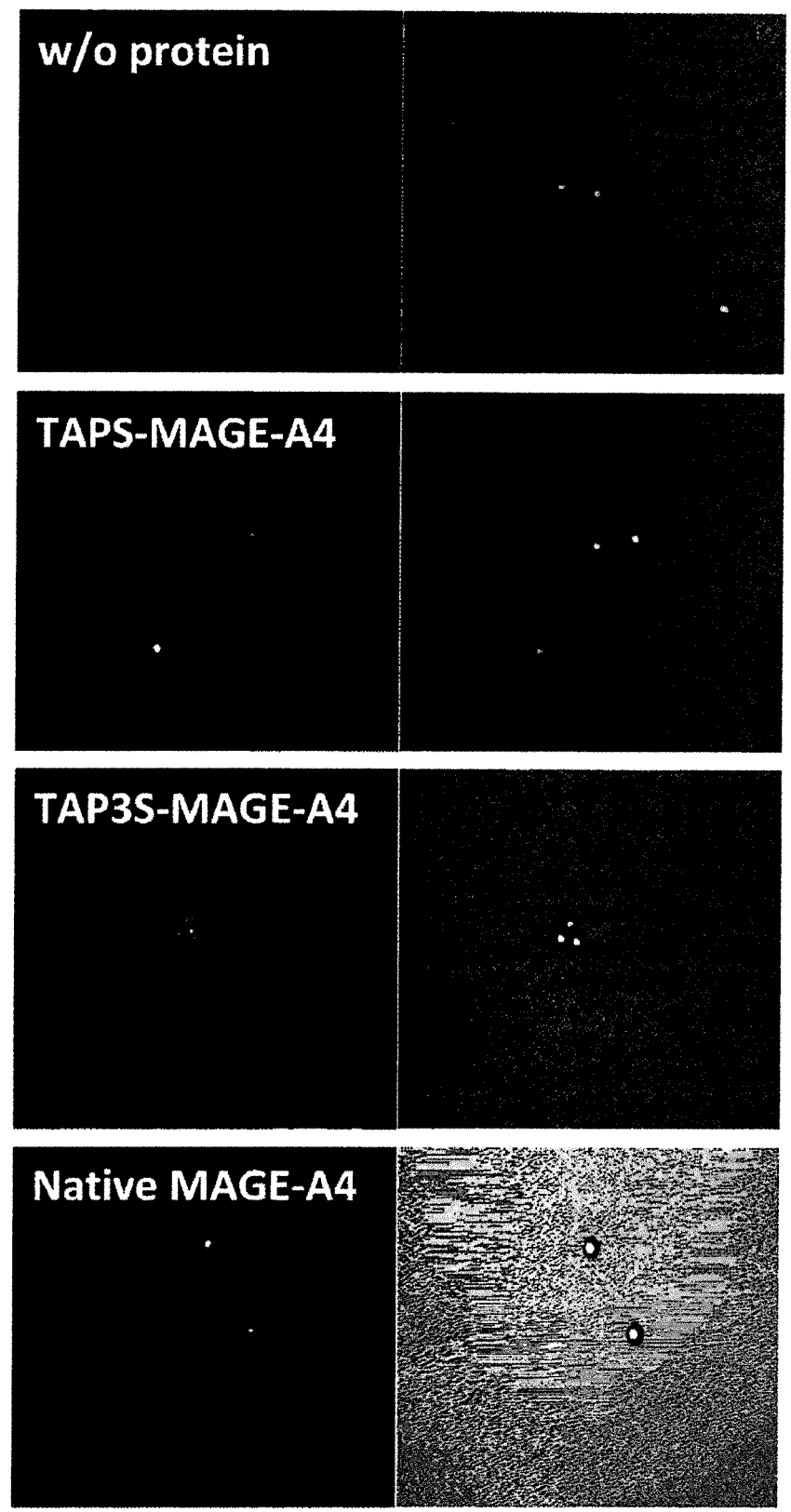
FIG. 14 provides images showing the detection of proteins bound with the surface of Bio-Plex COOH beads, TAPS-bound MAGE-A4-immobilized beads stored for 104 days, TAP3S-bound MAGE-A4-immobilized beads stored for 104 days, and native MAGE-A4-immobilized beads stored for 104 days. The left images are images taken by a confocal laser scanning fluorescence microscope. The right images are differential interference images (bright field) taken at the same time therewith.

An anti-His-tag antibody (OGHis, manufactured by Medical & Biological Laboratories Co., Ltd. (MBL)) diluted to 200 ng/mL in PBS was mixed with the beads of each type at room temperature for 30 minutes. Then, the beads were washed twice with PBS. Next, an anti-mouse IgG-Alexa 488 (secondary antibody; Invitrogen Corp.) diluted to 200 ng/mL in PBS was mixed with the beads of each type at room temperature for 30 minutes. Then, the beads were washed twice with PBS. These beads were observed under a confocal laser scanning fluorescence microscope (excitation light: 488 nm, fluorescence filter LP505) to visualize the presence of the His-tagged MAGE-A4 protein on the surface of the beads. The taken images are shown in FIG. 14. All of the images were taken with the same detection sensitivity. As shown in FIG. 14, the MAGE-A4 protein was confirmed to be bound with the surface of all of the beads.

The results of Example 5 demonstrated that the beads prepared by the method for producing a reagent for antibody detection disclosed in the present invention are more effective for inhibiting the formation of aggregates than beads prepared using a native protein. This inhibition of the formation of aggregates was also confirmed to be not attributed to the liberation of the antigenic protein from the bead surface. TAP3S is generally known to be superior in protein-solubilizing ability to TAPS. Unlike this solubilizing ability, however, the inhibitory effects on the aggregation of prepared beads were shown to be higher in TAPS.

Example 6

Protein Cationization Using TAP-Br

XAGE1b or NY-ESO-1 affinity-purified as described above was added to an eggplant-shaped flask, then dehydrated using a freeze dryer, and dissolved in 3 mL of 6 M guanidine and 0.1 M Tris-HCl (pH 8). After deaeration and nitrogen substitution, 30 mM DTT (solid) was added thereto, followed by treatment at 37° C. for approximately 1 hour. To the solution containing XAGE1b or NY-ESO-1, 70 mM TAP-Br was added, followed by treatment at 37° C. for approximately 60 minutes.

To the solution containing XAGE1b or NY-ESO-1 and TAP-Br, acetic acid in an amount of 1/10 thereof was added, and the mixture was then well dialyzed against Milli-Q water at 4° C. TAP-bound XAGE1b or NY-ESO-1 was purified by reverse-phase HPLC.

Beads on which TAP-bound XAGE1b, TAPS-bound XAGE1b, TAP-bound NY-ESO-1, and TAPS-bound NY-ESO-1 were respectively immobilized were prepared by the method described in Example 1. The TAP-bound antigenic protein was also confirmed to be successfully immobilized on the beads, as with the TAPS-bound antigenic protein.

All publications and patents cited herein are incorporated herein by reference in their entirety.

INDUSTRIAL APPLICABILITY

As described above, a reagent for antibody detection comprising an antigenic protein can be efficiently produced by use of the production method of the present invention. The reagent for antibody detection produced by the production method of the present invention was confirmed to be highly stable and also capable of efficiently detecting an antibody in a liquid sample. Use of the reagent of the present invention can provide an antibody analysis test that is free from the constraints of the HLA type of a subject. This test can probably be carried out, for example, to thereby decide a therapeutic strategy for a disease involving the immunity or to thereby predict or determine therapeutic effects on the disease.

The invention claimed is:

1. A reagent for detection of antibody binding to an epitope of an antigenic protein comprising
a suspension of magnetic beads and a cationized, denatured antigenic protein irreversibly immobilized on the magnetic beads,
wherein the cationized, denatured antigenic protein has cationized SH groups formed from reaction with a (3-bromopropyl)trimethylammonium (TAP-Br) cationizing agent.

2. The reagent for antibody detection according to claim 1, wherein the antigenic protein is a full-length protein.

3. The reagent for antibody detection according to claim 1, wherein the antigenic protein is a membrane protein.

4. The reagent for antibody detection according to claim 1, wherein the antigenic protein is a cancer antigenic protein.

5. A method for detecting an antigen-specific antibody contained in a sample, the method comprising the steps of:
contacting a reagent for antibody detection according to claim 1 with the sample;
adding thereto an antibody-binding labeled secondary antibody to allow the secondary antibody to bind to the antibody;
recovering the reagent for antibody detection; and
detecting the reagent for antibody detection bound with the antibody.

6. The method according to claim 5, wherein the sample is an isolated body fluid.

7. The reagent according to claim 1, wherein the cationized, denatured antigenic protein is immobilized on a surface of the magnetic beads through a reaction of an antigenic protein amino group with an activated carboxylic acid group on the surface of the magnetic beads.

8. A reagent for detection of antibody binding to an epitope of an antigenic protein comprising
   a suspension of magnetic beads and a cationized, denatured antigenic protein immobilized on the magnetic beads;
   wherein the cationized, denatured antigenic protein has cationized SH groups formed from reaction with an alkyl halide cationizing agent.

9. The reagent according to claim 8, wherein the cationized, denatured antigenic protein is immobilized indirectly on the magnetic beads via a biotin-avidin bond.

10. The reagent according to claim 8, wherein the alkyl halide cationizing agent is a (3-bromopropyl)trimethylammonium salt.

11. The reagent according to claim 8, wherein the cationized, denatured antigenic protein is irreversibly immobilized and indirectly bound to the magnetic beads via a linker molecule.

12. A method for detecting an antigen-specific antibody contained in a sample, the method comprising the steps of:
   contacting a reagent for antibody detection according to claim 8 with the sample;
   adding thereto an antibody-binding labeled secondary antibody to allow the secondary antibody to bind to the antibody;
   recovering the reagent for antibody detection; and
   detecting the reagent for antibody detection bound with the antibody.

13. The reagent according to claim 8, wherein the cationized, denatured antigenic protein is irreversibly immobilized on the magnetic beads.

* * * * *